(12) United States Patent
Newell et al.

(10) Patent No.: US 12,220,517 B2
(45) Date of Patent: Feb. 11, 2025

(54) BODY TEMPERATURE MEASUREMENT DEVICES, METHODS, AND SYSTEMS

(71) Applicant: NxStage Medical, Inc., Lawrence, MA (US)

(72) Inventors: Scott W. Newell, Ipswich, MA (US); Dennis M. Treu, Castle Rock, CO (US); Jerome James, Vestavia, AL (US)

(73) Assignee: NxStage Medical, Inc., Lawrence, MA (US)

( * ) Notice: Subject to any disclaimer, the term of this patent is extended or adjusted under 35 U.S.C. 154(b) by 82 days.

(21) Appl. No.: 18/195,999

(22) Filed: May 11, 2023

(65) Prior Publication Data
US 2023/0277745 A1    Sep. 7, 2023

Related U.S. Application Data

(60) Continuation of application No. 17/389,963, filed on Jul. 30, 2021, now Pat. No. 11,684,708, which is a division of application No. 16/387,715, filed on Apr. 18, 2019, now Pat. No. 11,090,424, which is a continuation of application No. 15/766,766, filed as application No. PCT/US2016/056198 on Oct. 8, 2016, now Pat. No. 10,668,206.

(60) Provisional application No. 62/268,511, filed on Dec. 17, 2015, provisional application No. 62/239,838, filed on Oct. 9, 2015.

(51) Int. Cl.
*A61M 1/36* (2006.01)
*G05D 23/19* (2006.01)

(52) U.S. Cl.
CPC .............. *A61M 1/367* (2013.01); *A61M 1/36* (2013.01); *A61M 1/3623* (2022.05); *G05D 23/1928* (2013.01); *A61M 2205/3372* (2013.01); *A61M 2230/50* (2013.01)

(58) Field of Classification Search
CPC ...... A61M 1/367; A61M 1/36; A61M 1/3623; G05D 23/1928
See application file for complete search history.

(56) References Cited

U.S. PATENT DOCUMENTS

| 3,094,482 | A  | 6/1963 | Vineyard |
| 5,866,015 | A  | 2/1999 | Kramer |
| 7,648,475 | B2 | 1/2010 | Cicco et al. |

(Continued)

FOREIGN PATENT DOCUMENTS

| CA | 2437090    | 10/2010 |
| EP | 1458432 B1 | 3/2008 |
| GB | 1569043    | 6/1980 |

OTHER PUBLICATIONS

Communication under Rule 71(3) dated Sep. 23, 2021 for European Patent Application No. 16854525.9.

(Continued)

*Primary Examiner* — Chester T Barry
(74) *Attorney, Agent, or Firm* — Potomac Law Group, PLLC

(57) ABSTRACT

A patient's body temperature measurement may be made by varying the heat transfer dynamics of a fluid exiting the patient's body and fitting parameters of heat transfer configuration to measurements under the varied conditions. Then the input temperature of the patient core can be extracted from the model and a current temperature measurement remote from the patient core and optionally other measurements such as fluid flow rate.

20 Claims, 13 Drawing Sheets

(56) References Cited

U.S. PATENT DOCUMENTS

| | | |
|---|---|---|
| 10,668,206 B2 | 6/2020 | Newell et al. |
| 11,090,424 B2 | 8/2021 | Newell et al. |
| 2002/0085952 A1 | 7/2002 | Ellingboe et al. |
| 2002/0104800 A1 | 8/2002 | Collins et al. |
| 2005/0094704 A1 | 5/2005 | Cicco et al. |
| 2006/0064025 A1 | 3/2006 | Kraemer |
| 2008/0058697 A1 | 3/2008 | Kamen et al. |
| 2008/0093312 A1 | 4/2008 | Holmes et al. |
| 2008/0156476 A1 | 7/2008 | Smisson et al. |
| 2012/0330117 A1 | 12/2012 | Grudic et al. |
| 2014/0299545 A1 | 10/2014 | Wrazel et al. |
| 2015/0204733 A1 | 7/2015 | Newell et al. |
| 2019/0240390 A1 | 8/2019 | Newell et al. |
| 2019/0247561 A1 | 8/2019 | Newell et al. |
| 2019/0247562 A1 | 8/2019 | Newell et al. |

OTHER PUBLICATIONS

Extended European Search Report dated Jul. 19, 2022 for European Patent Application No. 22159172.0.
Extended European Search Report dated May 23, 2019 for European Patent Application No. 16854525.9.
International Preliminary Report on Patentability for International Application No. PCT/US2016/056198 dated Apr. 10, 2018.
International Search Report and Written Opinion for International Application No. PCT/US2016/056198 dated Feb. 14, 2017.

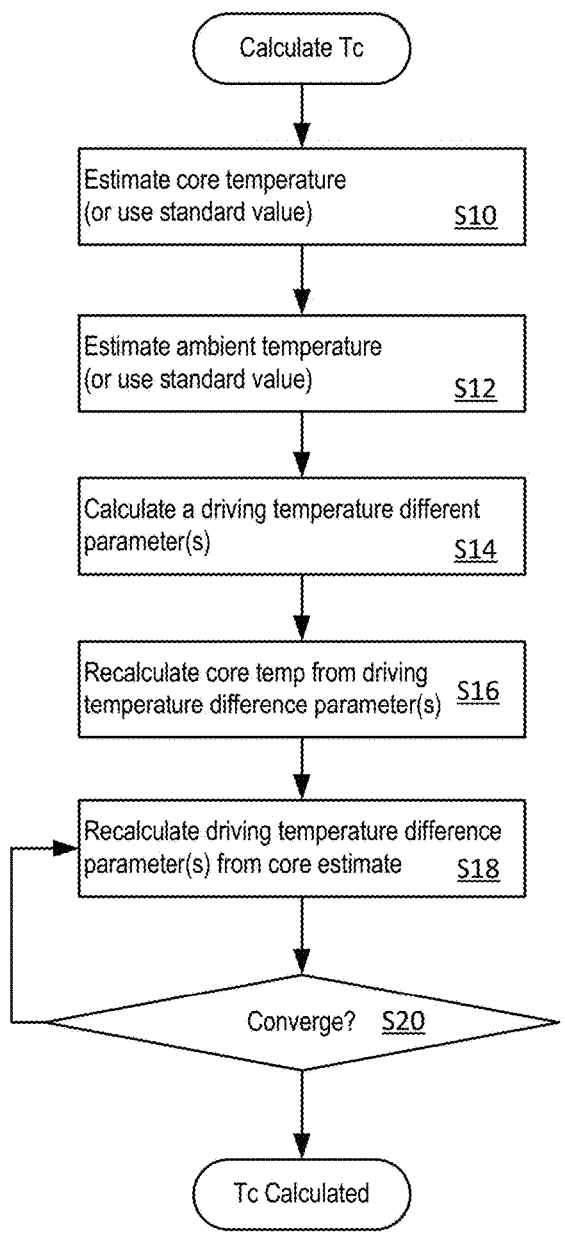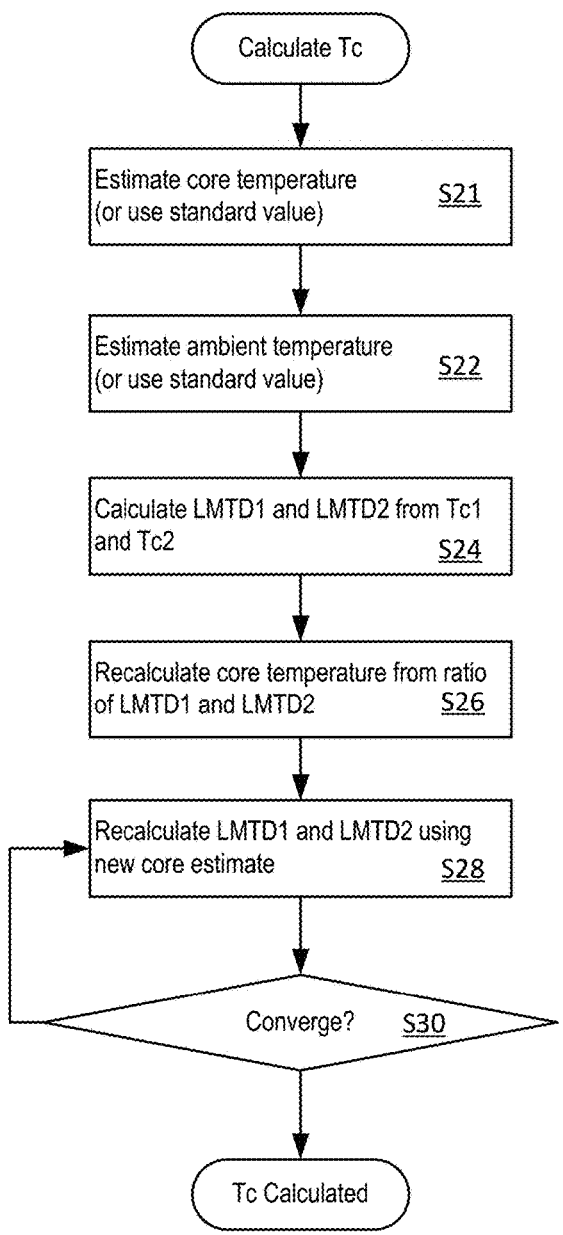
Fig. 3B                                  Fig. 3C $$Tpc = Ta + (Ta - Tb) * (L1/L2)$$

Fig. 14A (FD) = No flow (TD) = Normal body temp (Fb) = Normal treatment flow

Fig. 14B (TDi) → (Tv) = (Tp)  (FD) = Normal treatment flow
Using Xv = Xa

Fig. 14C ⋈ = bypass  (FD) = No flow

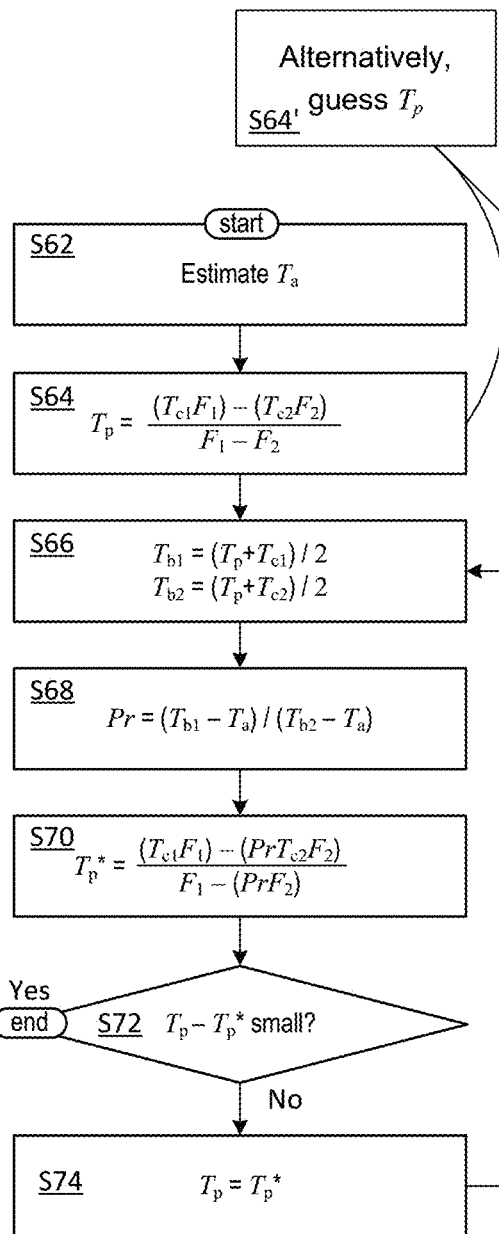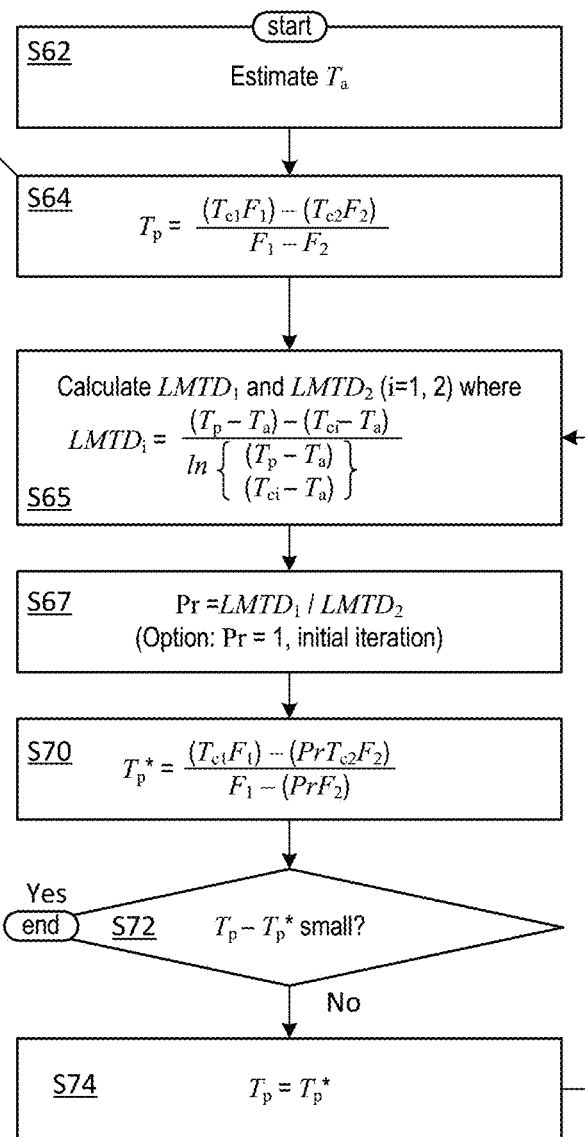
Fig. 15A                                Fig. 15B

BODY TEMPERATURE MEASUREMENT DEVICES, METHODS, AND SYSTEMS

CROSS-REFERENCE TO RELATED APPLICATIONS

This application is a Continuation of U.S. application Ser. No. 17/389,963, filed Jul. 30, 2021, which is a Divisional of U.S. application Ser. No. 16/387,715, filed Apr. 18, 2019, now U.S. Pat. No. 11,090,424, which is a Continuation of U.S. application Ser. No. 15/766,766, filed Apr. 6, 2018, now U.S. Pat. No. 10,668,206, which is a U.S. national stage filing under 35 U.S.C. § 371 of International Application No. PCT/US2016/056198, filed Oct. 8, 2016, which claims the benefit of U.S. Provisional Application No. 62/239,838 filed Oct. 9, 2015 and U.S. Provisional Application No. 62/268,511 filed Dec. 17, 2015, all of which are incorporated herein by reference in their entirety.

BACKGROUND

Extracorporeal blood treatments fall into a variety of categories ranging from blood oxygenation and therapeutic hypothermia to renal replacement therapies such as hemodialysis (HD). In extracorporeal blood treatments, such as HD, blood is pumped from a patient through a blood circuit and through a treatment device, such as a dialyzer. Toxins and electrolyte exchange across a dialyzer membrane to exchange with a treatment fluid. The exchange causes the removal of waste products in the blood and excess water. A substantial volume of the patient's blood may pass through an extracorporeal blood treatment system during the course of a treatment such that any heat transfer to or from the blood can upset the patient's body temperature. Systems are also known which are used to detect patient's core temperature to permit the control of the return temperature of the blood to ensure the patient's body temperature is properly controlled.

SUMMARY

In a principal application, a patient's body temperature is calculated responsively to a temperature of blood flowing through a blood circuit taken at an extracorporeal blood treatment component. Blood flows into an arterial line in extracorporeal blood circuit through one or more devices such as a treatment device, and back to a patient. A system, device, or method may measure a blood inlet temperature, which may be near, in magnitude, to the patient's core temperature using a sensor that is remote from the inlet. For example, the inlet may be at the patient access. The inlet temperature may be calculated from the temperature sensor indication in spite of a temperature change of the blood in the blood circuit due to heat gain or loss caused by heat transfer between the blood and the external environment of the blood circuit. For example, in a simple example, blood flows from a patient into a tube which exchanges heat with the surrounding ambient air, the air being at a temperature below a core temperature of the patient. As a result, the blood cools within the tube. If the heat transfer properties of the tube are known (that is the internal and external heat transfer coefficient, tube conductivity, and ambient temperature are known), the blood temperature can be inferred by calculation from a measurement of the blood at a point along the tube. This may be done by calculating the heat lost up to the point where the temperature is measured and thereby determining the temperature at a point before the blood reached the tube. However, such information may not be available particularly the temperature of the external environment. In addition, the latter may vary along the length of the circuit from the inlet to the temperature sensor.

Knowing the precise heat transfer conditions required to make such a calculation is difficult. This may be for a variety of reasons including manufacturing variability of the tube, variation in external temperature, imprecise values for heat transfer coefficients which are influenced by external forced convection as well as thermally-driven natural convection, etc. According to the disclosed embodiments, the temperature is measured at multiple flow rates and temperature readings for each condition are stored. Then these readings are used with a thermal model of the system to calculate the inlet temperature. In an embodiment, the heat transfer rate is the same for two flow rate conditions. This gives two unknowns (the heat transfer rate) and two equations allowing the inlet temperature to be calculated from the remote temperature readings and the flow rates, which are known. In embodiments this initial estimate of the inlet temperature can be improved by using an initial guess, estimate, or measurement of the ambient temperature to recursively calculate an improved estimate of the inlet temperature which may be used again to improve it until converged. In other embodiments the unknown parameters of inlet temperature heat transfer rate (power units) may be calculated using a brute force optimization method such as an annealing algorithm or Monte Carlo method. The latter may be preferred where the fluid temperature is modeled as an exponential (decay), for example using log mean temperature difference (LMTD). In further embodiments, the ambient temperature may be estimated by fitting three temperatures and three flow rates as knowns to a thermal model of the flow system. From the disclosure below, it should be evident that the principles and features of the disclosed subject matter may be applied to other fluid systems such as a pumped fluid system with a storage vessel, for example, or a blood system connected to a non-human animal.

In a method embodiment:

1. The temperature of blood flowing at a single point in the arterial line is measured after tracking for a steady state condition (i.e., zero change over time) at a first flow rate, for example, maximum blood flow and the temperature recorded.

2. Then, the above is repeated but with the flow rate at another flow rate, for example, 50% of maximum blood flow. These flow rates are examples and other flow rates can be used as long as they are different.

3. Next, assuming the heat transfer rate (power gain or loss) due to temperature differential between the fluid and ambient temperature is constant (i.e., constant heat transfer rate) at both blood flow rates, the patient blood temperature ($T_p$) is calculated from both temperatures according to $$Tp = \frac{T_{c1}F_1 - T_{c2}F_2}{F_1 - F_2}$$

where $T_{c1}$=Temp reading for full blood flow, $T_{c2}$=Temp reading for 50% blood flow, $F_1$=maximum flow rate, $F_2$=50% maximum flow rate. This is based on a single heat transfer rate (power units) in the channel so the rate of change in temperature is inversely proportional to the flow rate.

Instead of maximum flow rate or 50% flow rate, $F_1$ can be a known first flow rate and $F_2$ can be a known second flow rate where the second flow rate is approximately 50% of the first flow rate or some other fraction or multiple thereof. Again, any combination of one or more flow rates and any number of temperature measurements may be used to infer the core temperature from a variety of different thermal models of a system. Indirect temperature measurements of the target fluid (e.g., blood) may be made and used, for example, the temperature of spent dialysate leaving a dialyzer may be used instead of direct measurement of the temperature of the blood if the flow rates allow the assumption that the dialysate is near equilibrium with the blood. The analytical or numerical model to which the dialysate temperature is applied to infer the core temperature may appropriately represent the known and unknown thermal parameters of the system to permit the core temperature to be inferred.

The above estimate of inlet temperature can be refined by calculating a ratio of average temperature differences (blood and external temperature) based on a measured or estimated external temperature as discussed herein. The method can be further refined by using log mean temperature difference and even further refined by iteratively calculating an external (ambient) temperature. The terms external temperature, environment temperature, and ambient temperature are used interchangeably herein. Also the inlet temperature and core temperature effectively refer to the same target temperature value that is sought to be estimated using the disclosed subject matter.

It will be evident to those of skill in the art that the method employs an approximation of the heat loss that assumes the heat loss between the patient and the temperature sensor is such that the change in temperature along the arterial line is low relative to the temperature difference between the patient blood temperature and the ambient. In scenarios where that assumption does not apply, a suitable curve, such as an exponential decay function, can be fitted to multiple measured temperatures for a larger number of flow rates. The log mean temperature difference may be used, for example.

The approximation of the above method provides the advantage of requiring only two samples. Further the use of maximum and half-maximum flow rates can be provided during a typical treatment. The maximum flow rate may be a maximum safe flow rate with a safety margin such that said maximum is a reasonable rate for actual treatment. In further embodiments, temperature can be sensed along multiple segments of the arterial line and a single curve or line fitted to the multiple displaced segments. In each case, the fitted function may be used with known configuration data such as a physical spacing between multiple temperature samples to extrapolate the temperature at the patient. This method may not be as robust because it assumes the heat transfer characteristics of the paths between temperature sensors is related, in a known way—for example identical—and one of the temperature sensors and the inlet.

The method may be modified by providing other variables and basic assumptions about the flow system. For example, measurements of temperature at multiple points along the length of a blood circuit portion may be provided. The temperatures of parts of the flow circuit may be detected and used. Ambient temperature may also be used to refine estimates of the patient blood temperature. Alternately an ambient temperature may be stored based on predefined data or may be input by an operator to the controller or a standard value used.

According to embodiments, the temperature correction may be used to detect the core temperature of a patient, effectively correcting for the effect of heat exchange in the tubing from the patient to the temperature sensor. In embodiments, this corrected temperature is used to determine an abnormal patient core temperature, for example due to an inflammatory process which could occur during a treatment. In other embodiments, the corrected temperature may be used for negative feedback control of the return blood temperature to the patient.

Objects and advantages of embodiments of the disclosed subject matter will become apparent from the following description when considered in conjunction with the accompanying drawings.

BRIEF DESCRIPTION OF THE FIGURES

Embodiments will hereinafter be described in detail below with reference to the accompanying drawings, wherein like reference numerals represent like elements. The accompanying drawings have not necessarily been drawn to scale. Where applicable, some features may not be illustrated to assist in the description of underlying features.

FIGS. 3B and 3C are flow charts showing respective methods that can be implemented by a treatment machine controller, for example, to estimate patient core temperature from a temperature measurement remote from a patient or other subject.

FIGS. 14A-14C show sets of control conditions for measuring core temperature using the embodiments of FIG. 13 according to respective embodiments.

FIGS. 15A-15C are flow charts showing procedures for calculating patient core temperature according to respective embodiments of the disclosed subject matter.

DETAILED DESCRIPTION

Temperature measurement devices, methods, and systems for estimating a patient's core temperature from a temperature indicated at a point in a blood circuit remote from the patient's core may be employed in any type of blood circuit, including platelet extraction, therapeutic hypothermia, transfusion, blood oxygenation, renal replacement therapy or any type of extracorporeal blood treatment system. It will be evident that the methods, devices, and systems are applicable to any system in which a fluid, previously at equilibrium temperature with a patient's core, is drawn from a patient's body. Examples of fluid other than blood may include peritoneal dialysate, urine, or ultrafiltrate from an implanted artificial kidney.

Figure 1:
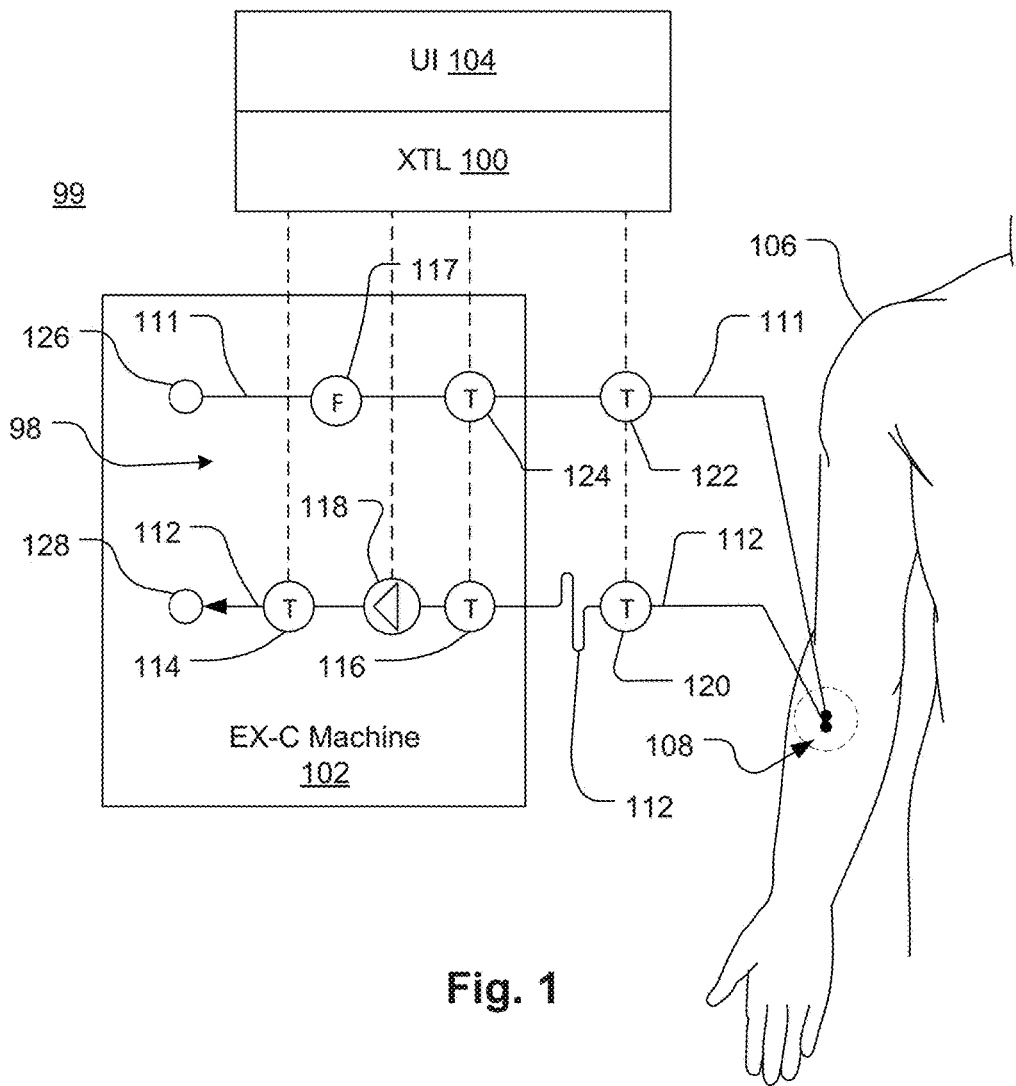
FIG. 1 shows an extracorporeal blood processing machine with a blood circuit and other components for completing a blood temperature measurement and performing a blood treatment.

Referring to FIG. 1, an extracorporeal blood treatment system 99 includes a blood treatment system 99 that includes an extracorporeal blood processing machine 102 that engages a blood circuit 98. The blood circuit 98 has an arterial blood line 112 and a venous blood line 111. The former is used to convey blood from a patient 106 via a patient access 108. The latter is used to return blood that has been treated by the extracorporeal blood processing machine 102 back to the patient 106 via the patient access 108. The blood circuit 98 transfers blood between the patient and the extracorporeal blood processing machine 102 as indicated figuratively by fluid connections 126 and 128. Note that portions of the blood circuit may reside within the extracorporeal blood processing machine 102. The connections 126 and 128 may transfer blood to and from a dialyzer, oxygenator, adsorbent, or some other component or components of the extracorporeal blood processing machine 102 thereby to perform a treatment. A blood pump 118 may engage the blood circuit 98 to pump blood therethrough. The blood circuit 98 may be a replaceable disposable component. One or more temperature sensors 114, 116, 120, 122, 124 may be arranged to measure a temperature of the blood at respective points along the blood circuit 98. A controller 100 has a user interface 104. The controller receives temperature signals from the one or more temperature sensors and controls the pump 118. In embodiments, the flow rate of blood may be directly measured by a flow sensor 117. The direct flow measurements may be applied in the calculation of patient core temperature as discussed below.

In embodiments, a single temperature sensor is located at the extracorporeal blood processing machine 102 in the arterial line, for example as indicate at 114 or 116. In other embodiments multiple sensors may be used, each at different positions along the blood line. For purposes of the discussion immediately below, an embodiment using a single temperature sensor 116 will be described. The temperature sensor 116 may be of a type that measure blood temperature by providing a temperature sensor in contact with the outside of a flow channel that forms part of the blood circuit 98 arterial line 112. The temperature sensor 116 may further be of a type that actively detects and controls to minimize a flux of heat between the contents of the flow channel and the external sensor through negative feedback control. This type of temperature sensor, an active temperature sensor, is described in international patent application published as WO2014018798 to Newell.

In some embodiments employing the external sensor described in the above-cited international patent publication, a temperature sensor is included with a vessel/channel that has a temperature detecting device. A first temperature sensor can be attached to or placed against a wall of a vessel/channel and is configured for carrying or containing a fluid. A second temperature sensor can be separated from the first temperature sensor by an insulating body having a thermal resistance similar to the vessel/channel wall. There can be a temperature regulating device in thermal contact with the second temperature sensor and configured to receive first and second temperature indication signals, respectively, from the first and second temperature sensors. The temperature regulating device can be further configured to minimize a difference in temperatures indicated by the first and second temperature signals by regulating a rate of flow of heat between the first and second temperature sensors to prevent a flow of heat between the fluid (in this case, blood) and one or both temperature sensors. The regulating device may include an electrical resistance heater.

Figure 2:
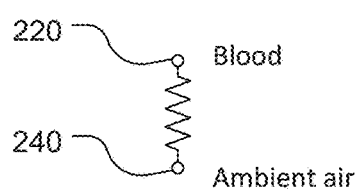
FIG. 2 illustrates an embodiment of a heat transfer model, according to embodiments of the disclosed subject matter.

The active temperature sensor described above is one type of temperature sensor that produces very accurate measurements of fluid temperature. A problem with these types of sensors is that they are not practical to locate close to the patient and therefore temperatures measured with them may be biased due to transfer of heat from the fluid circuit leading from the patient or other subject to the sensor. The disclosed embodiments estimate a correction for this bias permitting an accurate measurement of core temperature to be obtained. The blood circuit 98 may inevitably transfer heat from the environment to or from the blood flowing through it. This may cause a difference between the blood temperature leaving the patient 106 and the blood temperature measured at the temperature sensor 116. This may be mitigated by providing a temperature sensor right at the patient 106 access 108, however for precise temperature measurement as in the active temperature sensor 116 describe above, for practical reasons that should be apparent, it is difficult or costly to provide a disposable blood circuit 98 that can support the active temperature measurement configuration. This type of sensor is much more suitably provided on the extracorporeal blood processing machine 102. As a result, there will be a length of flow channel (typically tubing) leading from the patient 106 access 108 to the temperature sensor 116. Referring to FIG. 2, heat transfer to the surrounding environment 204, such as the ambient air, between the blood 204 carried in the length of arterial line 112 upstream of the temperature sensor 116 results in a difference across a thermal resistance which creates a difference in the temperature of blood leaving the patient 106 and the temperature measured at the temperature sensor 116.

In a principal application, a patient's body temperature is calculated responsively to a temperature of blood flowing through a blood circuit taken at an extracorporeal blood treatment component. Blood flows from an arterial line in extracorporeal blood circuits. The disclosed subject matter may compensate for a temperature change in the arterial line due to heat gain or loss depending on temperature difference and, optionally other factors, between the fluid circuit environment and the blood flowing in the arterial line. The resulting compensation, which may be generated computationally with a processor, may then be used to calculate a core temperature as indicated by the temperature of the blood leaving the patient's body. It should be evident that the principles and features of the disclosed subject matter may be applied to other fluid systems such as a pumped fluid system with a storage vessel, for example, or a blood system connected to a non-human animal.

In a method employing a linear extrapolation of the blood temperature leaving the patient 106:

1. The temperature of blood flowing at temperature sensor 116 in the arterial line 112 is measured after tracking for a steady state condition (i.e., zero change over time) at maximum blood flow and the temperature recorded. The controller 100 may automatically control the blood pump 118 to effect the desired blood flow. The blood flow rate may be determined by the controller according to parameters entered in the user interface 104.
2. The operation 1, above, is repeated but with the flow rate at 50% of maximum blood flow which may also be selected by the controller 100. Other percentages than 50% may be employed as well.
3. Next, the controller 100 calculates the patient blood temperature ($T_p$) from both temperatures according to $$Tp = \frac{T_{c1}F_1 - T_{c2}F_2}{F_1 - F_2} \quad (1)$$

where $T_{c1}$=Temp reading for full blood flow, $T_{c2}$=Temp reading for 50% blood flow, $F_1$=maximum flow rate, $F_2$=50% maximum flow rate. This assumes a single heat transfer rate (power units) in the channel so the rate of change in temperature is inversely proportional to the flow rate. In alternative embodiments, a curvilinear extrapolation of the blood temperature at the patient 106 may be used.

Instead of maximum flow rate or 50% flow rate, $F_1$ can be a known first flow rate and $F_2$ can be a known second flow rate where the second flow rate is approximately 50% of the first flow rate.

Using the above-described method, a temperature loss/gain can be estimated for an extracorporeal blood treatment. A first temperature at a first flow rate can be measured at a temperature sensor. A second temperature at a second flow rate can be measured at the temperature sensor. A patient blood temperature can be found based on the first and second temperatures and first and second flow rates. The patient blood temperature can be compared to a third temperature at a third flow rate, where the third flow rate can be a normal flow rate of the machine for the particular patient or for a particular treatment. Temperature gain or loss can be used to estimate a corresponding temperature loss or gain at a fluid temperature regulator. As further described below, temperature gain or loss can further be estimated for the return part of the blood circuit between the temperature sensor and the patient. The estimated temperature gain or loss for the return part of the blood circuit can be used by a fluid temperature regulator to heat or cool the fluid by an amount determined to counteract the gain or loss of the circuit, i.e., heat or cool the fluid to by a temperature equal to the sum of the temperature loss or gain estimated for the supply of the blood circuit to the temperature sensor and the temperature loss of gain estimated for the return of the blood circuit from the temperature sensor to the patient. In addition, the temperature of return blood may be reduced to by a predefined temperature interval to help control a fever. The return temperatures for given fever levels may be stored by a system controller and used to control a heating apparatus that controls the temperature of blood returned to the patient.

Figure 3A:
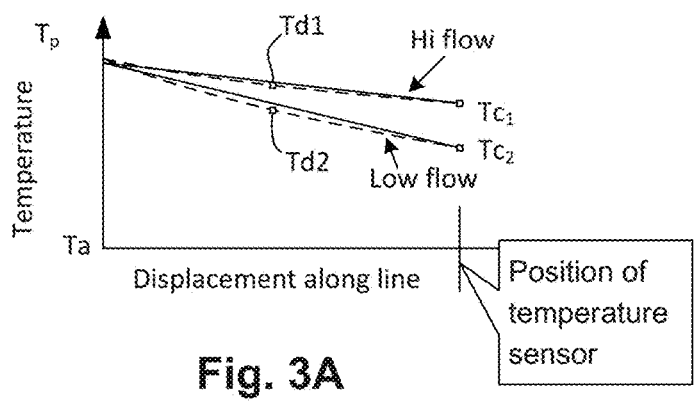
FIG. 3A shows a graph of blood temperature versus displacement of blood along a flow channel, according to embodiments of the disclosed subject matter.

Referring to FIG. 3A, a graph illustrates how the temperature of the blood may decay exponentially (dashed lines) as it is displaced along the length of arterial line 112 between the access 108 and the temperature sensor 116. The two curves illustrate how the decay rate is faster at a low flow rate compared to a higher flow rate. $T_p$ is an extrapolated temperature of the blood leaving the patient generated by extrapolation according to respective embodiments. The extrapolation may be done by various means as discussed below. In embodiments in which a linear extrapolation of the blood temperature leaving the patient is performed, temperature may be measured at a single point along the arterial line. In other embodiments, the temperature measurement may be made at multiple points (not illustrated here). A curvilinear extrapolation or a model of the heat transfer that takes account of the exponential decay may be used. A non-exponential model may also be used such as an arbitrary fittable function such as a polynomial function. In embodiments, the function is selected to model the thermal behavior of the system such as an exponential decay function which represents a model of the transfer of uniform heat from or to a tube with a flow and uniform heat transfer U-value (W/m²K) along the tube. The dotted lines show the exponential decay of the temperature assuming the ambient temperature $T_a$ outside the arterial line 112 is lower than the blood temperature. The graph also illustrates that the temperature change of blood from the point where it leaves the patient at temperature $T_p$ and the point or points where it is measured (intermediate points Td1, Td2) $T_{c1}$, $T_{c2}$. The temperature change may be a minor fraction of the temperature difference between the blood temperature and the ambient temperature $T_a$ so that the approximation of equation 1 holds. The latter condition makes the linear approximation described above reasonable and allows two temperature measurements at two flow rates to be used to extrapolate a very accurate temperature estimate for blood leaving the patient. An exponential model that may be fit to several temperature data points is:

$$T_c = T_a + (T_p - T_a)e^{\left[-\frac{X_L L}{Q}\right]} \quad (2)$$

Where $T_c$ is a temperature of the fluid measured at position L distance from the input fluid at temperature $T_p$, Q is the flow rate, $T_a$ is the ambient temperature, and $X_L$ is a lump parameter=$UC/c_p\rho$ where U is an overall U-value that accounts for heat transfer resistance, C is the circumference of the tube taken at the radius upon which the U-value is derived, and $c_p\rho$ is the product of the fluid specific heat and density. The exponential may be fitted to solve for $T_a$ and $X_L$ using multiple temperatures at multiple distances along the tube, multiple flow rates, or a combination. The temperatures may be oversampled and applied to regression. Multiple temperatures will be of limited use in the context of blood temperature measurement because the heat transfer properties (outside temperature, adventitious insulation or heat sources such as caused by contact with person or bed, etc.) of the respective circuit portions between the temperature sensors are likely to be different and unpredictable.

Referring to FIG. 3B, the estimate given by equation 1 can be improved by using the estimate for the patient temperature $T_p$ S10 from equation 1 or similar calculation as discussed elsewhere and an estimate, or approximation, of the ambient temperature S12 to calculate temperature difference parameters S14 for the flow at each flow rate. In addition, alternatively, the initial calculation of $T_p$ can be skipped and a standard value used instead. Using these temperature parameters, the ratios of the rate of heat loss for the flows at the two flow rates can used to solve for a new estimate of the patient core temperature S16. See equation 3a where TDPi represents a temperature parameter for the flow rate i. An example of a temperature difference parameters is the average of the core and measured temperatures minus the ambient temperature estimate ($T_{bi}$ as given by equation 3b) may be used.

$$T_p = \frac{T_{c1}F_1 - \left(\frac{TDP_1}{TDP_2}\right)T_{c2}F_2}{F_1 - \left(\frac{TDP1_1}{TDP_2}\right)F_2} \quad (3a)$$

$$T_{bi} = \frac{(T_p + T_{ci})}{2} - T_a \quad (3b)$$

$$T_p = \frac{T_{c1}F_1 - \left(\frac{T_{b1}}{T_{b2}}\right)T_{c2}F_2}{F_1 - \left(\frac{T_{b1}}{T_{b2}}\right)F_2} \quad (3c)$$

The recalculated core temperature $T_p$ can then be used to derive a new estimate of the temperature difference parameters S18 and the core temperature recalculated. For example, if the average temperature difference ($T_{bi}$) is used this would be plugged into equation 3a to give the updated $T_p$ as in equation 3c. The update can be iterated until $T_p$ converges S20 or for a fixed number of iterations. Other termination conditions can also be used such as a variable number of iterations that corresponds to the difference in the flow rates $F_1$ and $F_2$.

Referring to FIG. 3C, a particular example employs the log mean temperature difference (LMTD) which is a temperature difference based on the assumption of the exponential decay of temperature in a tube carrying a fluid. It will be understood that the ratio of the $F_1$ flow rate multiplied by the temperature change of the blood from the patient to the temperature sensor to the corresponding temperature change at the $F_2$ flow rate multiplied by that flow rate is equal to the ratio of LMTDs at the corresponding flow rates. That is:

$$\frac{LMTD_1}{LMTD_2} = \frac{(T_p - T_{c1})F_1}{(T_p - T_{c2})F_2} \quad (3d)$$

where LMTD is given by:

$$LMTD = \frac{(T_p - T_a) - (T_{ci} - T_a)}{\ln(T_p - T_a) - (T_{ci} - T_a)} \quad (3e)$$

Where $T_a$ is an estimate for the ambient temperature and $T_{ci}$ is the measured value for the flow rate I (=1 or 2). The ambient temperature $T_a$ can be directly measured or a standard value used. If an estimate or measurement of the ambient temperature $T_a$ and an initial estimate for $T_p$ from equation 1 (S21) are plugged into equation 3 (S24), then equation 4, which is equation 3 rearranged, can be used to solve for an improved estimate of $T_p$ S26. Then the LMTD ratio can be solved again S28 and this process iterated using increasingly better estimates of $T_p$ until it converges S30 or a fixed number of iterations is carried out.

$$T_p = \frac{T_{c1} - \left(\frac{LMTD_1}{LMTD_2}\right)T_{c2}F_2}{F_1 - \left(\frac{LMTD_1}{LMTD_2}\right)F_2} \quad (4)$$

Figure 3D:
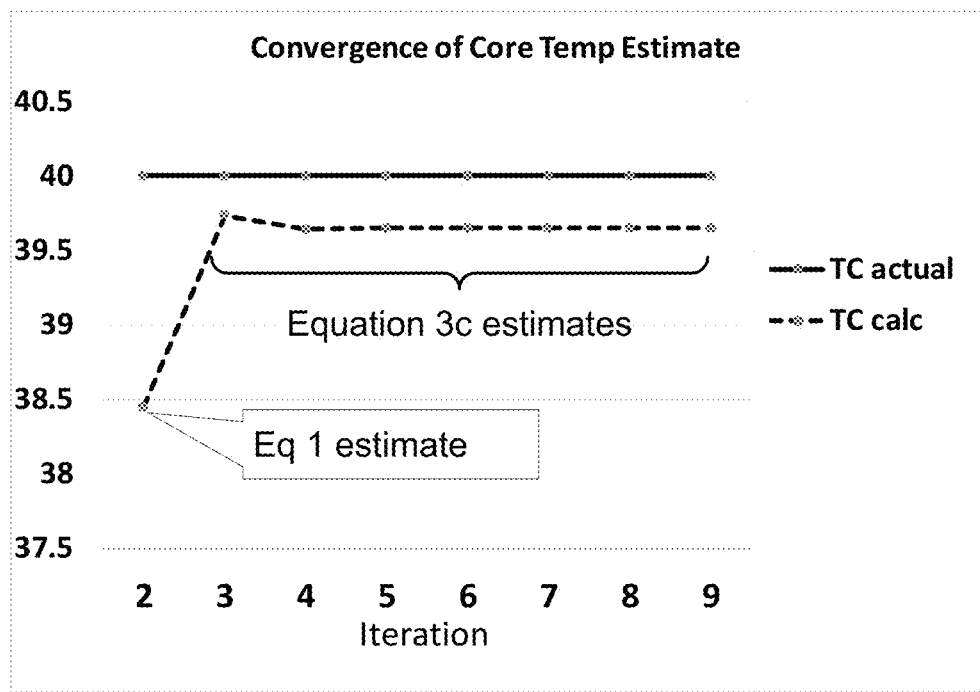
FIGS. 3D and 3E show a result of a simulation of the method of FIGS. 3C and 3D, respectively.
Figure 3E:
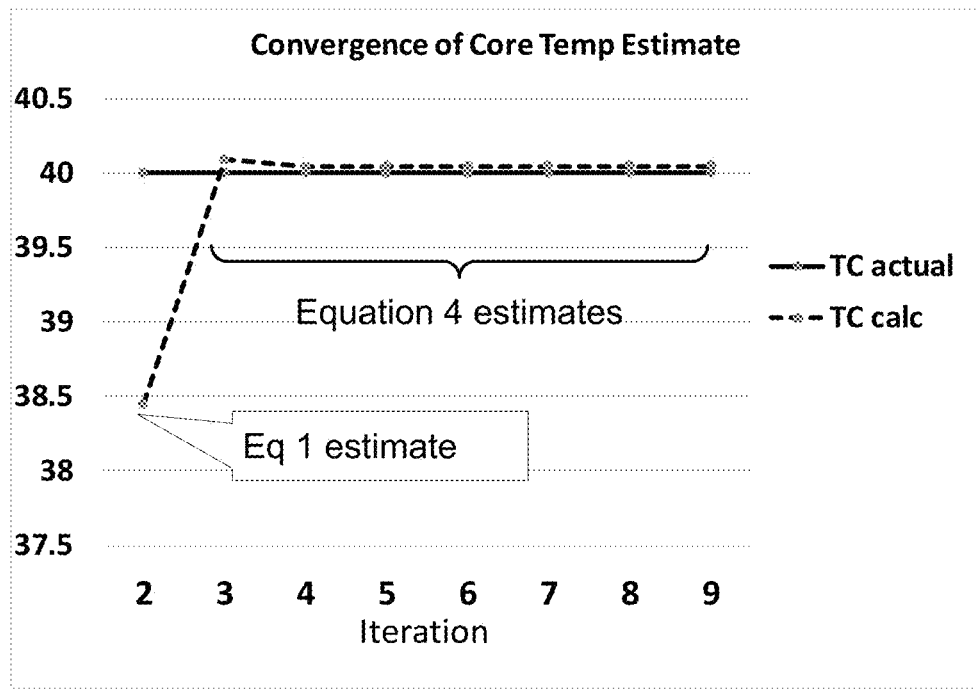

FIG. 3D shows the results of using the estimation procedure of FIG. 3B with a simulated fluid flow calculated from a patient temperature of 40 and flow rates of 100 and 200 ml/min and $T_{c1}$ and $T_{c2}$ of 36.5 C and 33.8 C, respectively. A constant UA and L were used. The results show that $T_p$ converged within 4 iterations to a value that is close to the ground truth value of 40. FIG. 3D shows the results of using the estimation procedure of FIG. 3C with a simulated fluid flow calculated from a patient temperature of 40 and flow rates of 100 and 200 ml/min and $T_{c1}$ and $T_{c2}$ of 36.5 C and 33.8 C, respectively. A constant UA and L were used. The results show that $T_p$ converged within 4 iterations to a value that is close to the ground truth value of 40.

Figure 4:
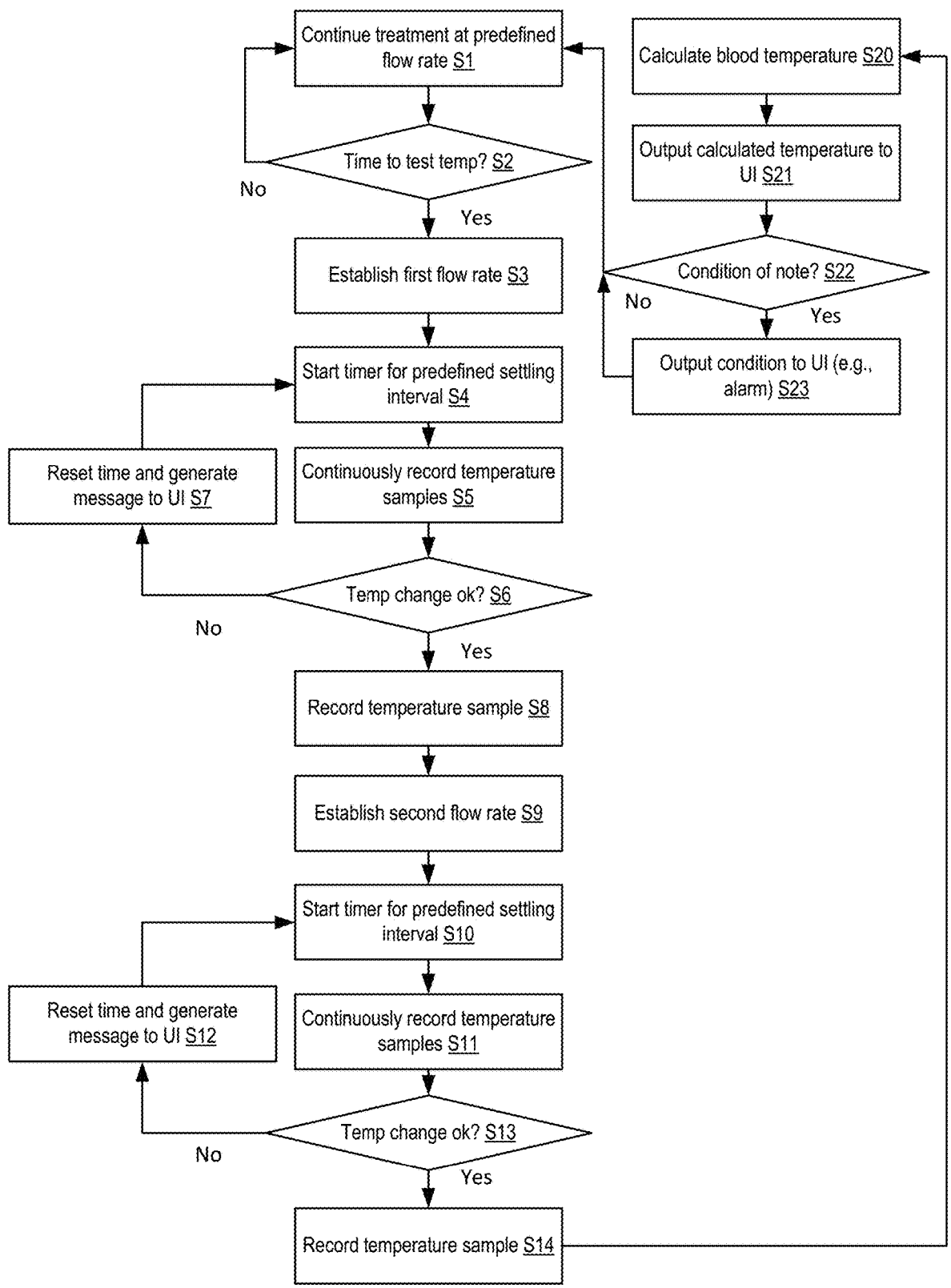
FIG. 4 shows a method of determining and employing blood temperature for detecting a patient condition, according to embodiments of the disclosed subject matter.

Referring to FIG. 4, according to a method, a treatment process is underway at S1 in which blood is circulated from a patient through a blood treatment system and back to the patient as described, for example, with reference to FIG. 1. At a time selected by a controller, at S2, a test interval is initiated which begins by establishing a predefined first flow rate of the blood. The flow rate is established at S3. To ensure the heat transfer reaches a near-steady state condition, a watchdog timer may be initialized at S4. Alternatively, or in addition, the temperature (e.g., at 116) may be sampled (S5) by the controller which may wait for a constant or near-constant (unchanging over time within a predefined temperature interval stored by the controller) temperature at the sensor (e.g., 116). If the temperature variation is outside a predefined range, for example it fails to settle to a steady state, this may be detected at S6 by comparing the profile established by the samples recorded at S5 to a predefined requirement stored in the controller and a user interface message output at S7 with reversion to S4. If the temperature profile is satisfactory at S6, a temperature is recorded (or the latest one or more samples recorded) at S8. At S9, a second predefined flow rate is established. Again, to ensure the heat transfer reaches a near-steady state condition, a watchdog timer may be initialized at S10. Alternatively, or in addition, the temperature (e.g., at 116) may be sampled (S11) by the controller which may wait for a constant or near-constant (unchanging over time within a predefined temperature interval stored by the controller) temperature at the sensor (e.g., 116). If the temperature variation is outside a predefined range, for example it fails to settle to a steady state, this may be detected at S13 by comparing the profile established by the samples recorded at S11 to a predefined requirement stored in the controller and a user interface message output at S12 with reversion to S10. If the temperature profile is satisfactory at S13, a temperature is recorded (or the latest one or more samples recorded) at S14. The controller then calculates, at S20, a blood temperature leaving the patient, for example, using the linear extrapolation indicated above. The temperature may be output through a user interface S21. The temperature may be compared to a time profile or predefined temperature to determine if there is an abnormal condition such as a fever at S22 and if so, the condition detected may also be output at the user interface at S23. Control returns to S1.

A modification of the method of FIG. 4, which may be used with any of the embodiments, is to add a sequence in which the first flow rate is reestablished and the temperature reading performed again. This additional temperature reading may be used to confirm that the steady state conditions existed since the first measurement at the first flow rate and thereby confirm that the temperatures at the first and second flow rates are valid. Also, if any drift in the heat transfer conditions between the two first flow temperature measurements is linear, then taking an average of the two first flow temperature measurements would be representative of the conditions at the time the second temperature measurement was made. So, if $T_{c3}$ is the third temperature measurement at $F_1$, in the equations presented herein, $T_{c1}$ is simply replaced with an average of $T_{c1}$ and $T_{c3}$ in the new embodiments.

The core temperature data may be recorded in a treatment log and connected to a patient profile. The core temperature data may be recorded as a temperature vs. time log profile for each treatment. The profile over many treatments may be used as a reference in order to identify an abnormal profile for the patient. The temperature data may be stored by a treatment machine controller (remotely or locally) and used to output an indication that an abnormal condition exists by comparing standardized normal profile range with a current profile during a treatment.

Figure 5:
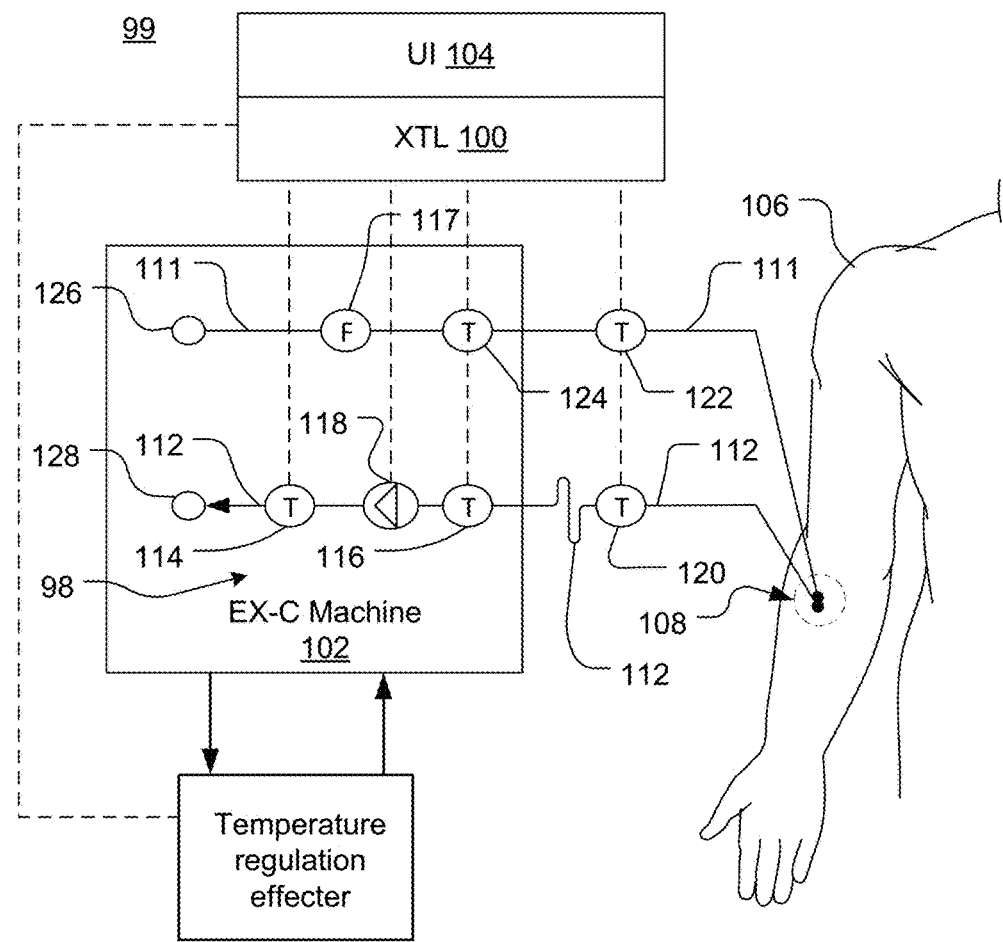
FIG. 5 shows an extracorporeal blood processing machine with a blood circuit and other components for completing a blood temperature measurement and performing a blood treatment with temperature regulation of return blood, according to embodiments of the disclosed subject matter.

FIG. 5 shows a system that is mostly identical to that of FIG. 1 except that is shows a temperature regulation effecter 140 which adds heat to the blood prior to returning the blood to the patient 106. In embodiments, the temperature regulation effecter 140 may be a fluid warmer that is controlled to regulate the temperature of returning blood to a target temperature as indicated by a temperature sensor monitoring the temperature of blood in the venous line 111. In embodiments of a dialysis system, this temperature regulation may be done by warming the dialysate prior to contacting the dialyzer where it warms the blood. In alternative embodiments, other methods and devices for warming blood, alone or in combination, may be employed to add heat to the blood or the patient's body directly or indirectly. A blood warmer may be employed, preferably one with low current loss such as an infrared radiant heater with electrical field isolation. In other embodiments, a convective warmer such as one that separates an electrical heat source from blood by circulating an intermediate heat transfer fluid between a blood circuit and a heater, for example, air or oil. A heating pad applied to a part of the patient with good circulation such as the thighs, abdomen or neck or any other suitable body part may also be used. In many embodiments, the manner of providing heat to the blood or the body can be of any suitable form.

Figure 6:
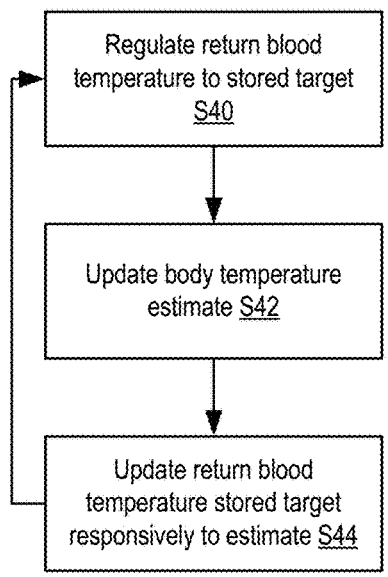
FIG. 6 shows a method applicable to the embodiment of FIG. 5, according to embodiments of the disclosed subject matter.

FIG. 6 shows a method for regulating the return blood temperature. A target temperature is stored by a controller (e.g., 100). The target is used to regulate the return blood temperature at S40 for example by negative feedback (using venous line temperature sensor) control of the venous line temperature. The patient blood temperature is obtained according to any of the methods described above through extrapolation at S42 and used to update the stored target at S44. This updated target is then used for regulation of the return blood temperature. The target may be extrapolated backwards using the temperature difference between arterial temperature at 116 and the extrapolated temperature such that the target is set equal to that difference added to the extrapolated temperature of the blood leaving the patient. This would fit the circumstance of heat loss in the venous line being equal to the heat loss in the arterial line, both between the patient the respective temperature sensor. In addition, the same method will apply when the patient target core temperature to be achieved is above or below a current temperature or normal temperature (forced body temperature) through the net withdrawal of heat or net supply of heat. The target temperature may be a therapeutic temperature as for some types of procedures such as surgical procedures or treatment of injuries where the body temperature is lowered or raised (e.g., concussion treatment). In addition to the forced body temperature approach described above, the method of FIG. 4 may be implemented to determine whether a fever exists prior to forcing the temperature or at intermediate points for diagnostic purposes.

A problem with core temperature measurement in certain systems such as extracorporeal blood circuits is that such systems often need to heat blood of a patient to desired return temperature upon reinfusion to keep the temperature of the patient at a desired level. To do this, heat may be transferred to the returning blood, which is generally cooled by passing through the treatment system. Of course a problem with this is that the active temperature regulation system that accomplishes this function of returning blood at a desired temperature will disrupt the natural temperature of the patient and prevent the temperature measurement process described herein from being diagnostically useful.

One device for mitigating the above problem is to measure the patient's temperature, using the presently-disclosed methods, devices, and systems, immediately after the first blood is drawn and before the patient's body temperature is affected by the temperature control system. See FIG. 8 and attending discussion for description of an embodiment. Another device for compensating the above problem is to monitor core temperature continuously and to detect a change in blood temperature that might be a diagnostic indication such as a patient fever. In the latter method, the controller may trigger a diagnostic signal upon detecting a predefined rate of change of core temperature at a time that blood return temperature and flow rate are held constant and blood outlet temperature remained steady for a predefined period of time indicating a change in the patient's temperature homeostasis set-point. Others are described with reference to FIGS. 13 and 14A-14C.

Figure 8:
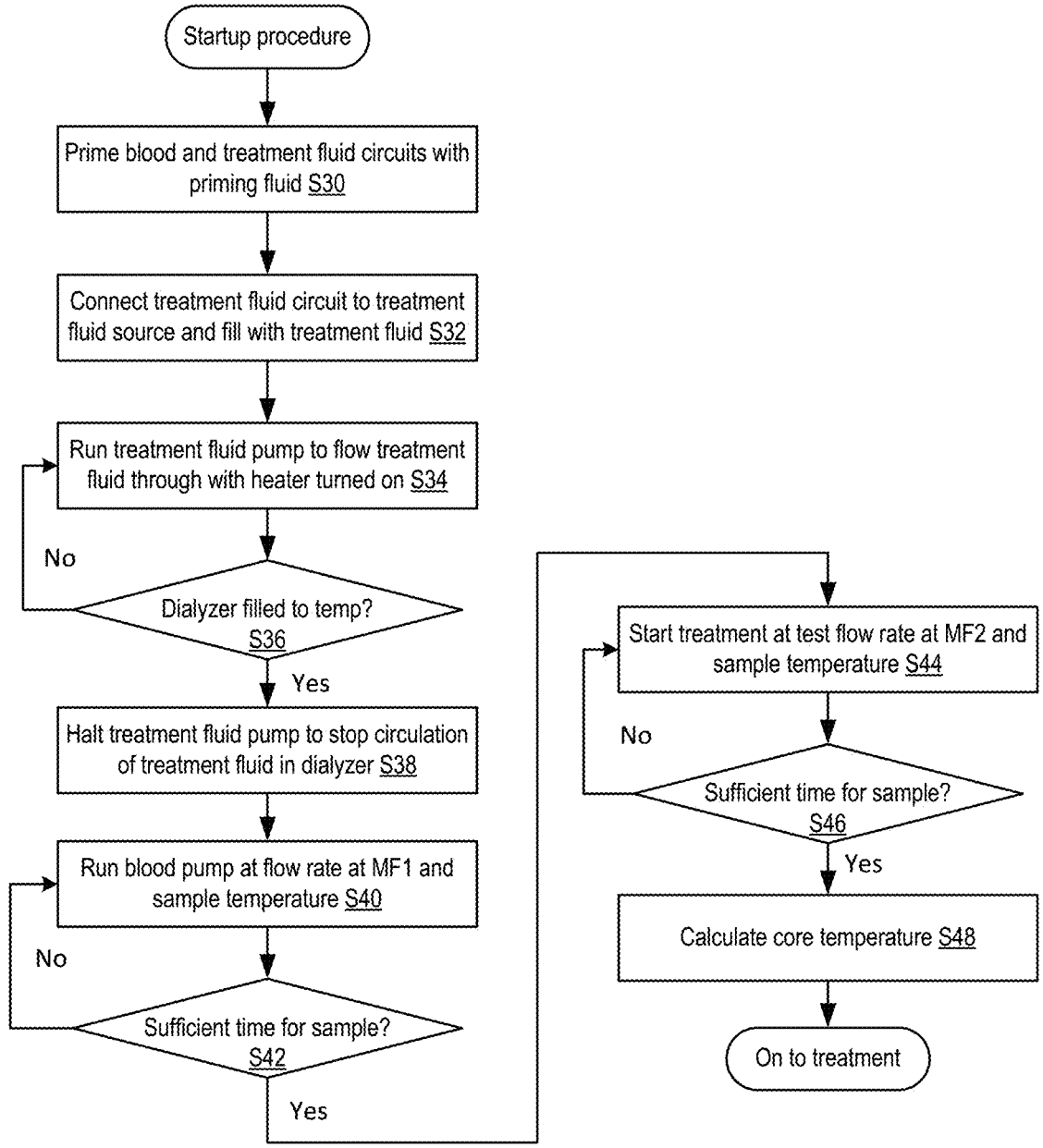
FIG. 8 shows a flowchart of a temperature measurement process that occurs during a temperature measurement phase of a startup mode of a blood treatment device such as a dialysis system.

FIG. 8 shows a flowchart of a temperature measurement process that occurs during a temperature measurement phase of a startup mode of a blood treatment device such as a dialysis system. The process is applicable to a system such as a dialysis system where there is a blood circuit that interfaces with a treatment fluid circuit to transfer heat therebetween through a treatment device such as a dialyzer. A startup mode includes a priming procedure during which the treatment fluid and blood circuits are primed S30. A variety of procedures are known for filling and optionally flushing blood and treatment fluid circuits and the details are not relevant here.

At S32, if necessary depending on the priming procedure used, the treatment fluid circuit is connected to a source of treatment fluid. For example, a dialysate circuit may be connected to a dialysate source. At S34 the treatment fluid is flushed through the treatment device while regulating its temperature by controlling a temperature regulator such as a heater. A flow is established through the treatment device (e.g., dialyzer) until the treatment fluid compartment is at a predefined temperature. The temperature may be, for example, a normal body temperature representative of the temperature of an afebrile subject. The treatment fluid is flushed at a sufficient rate in combination with a sufficient period of time (or total volume) such that the fluid compartment is estimated to be at the constant predefined temperature throughout. The time and rate may be predetermined, for example, a sufficient volume may be flushed at the predefined temperature to displace the internal treatment fluid compartment volume three times over. After this has been done, determined at S36, the treatment fluid pump is halted and a no-flow condition is established in the treatment fluid circuit compartment S38.

At S40, the blood pump operates to establish the first flow rate ($F_1$) for temperature measurement. This is done for a sufficient time S42 to reach a steady state heat transfer condition. The temperature indicated by the temperature sensor ($T_{c1}$) is recorded. At S44, the blood pump operates to establish the second flow rate ($F_2$) for temperature measurement. This is done for a sufficient time S46 to reach a steady state heat transfer condition. The temperature indicated by the temperature sensor ($T_{c2}$) is recorded. Then the controller calculates the temperature from the two temperature readings and the flow rates S248 as described herein according to any of the embodiments. The process may be done with multiple flow rates and temperature readings even though the conditions may be considered to be oversampled and an average of the estimations at the multiple combinations of flows and temperature readings may be taken as a best estimate of the core temperature.

Figure 9:
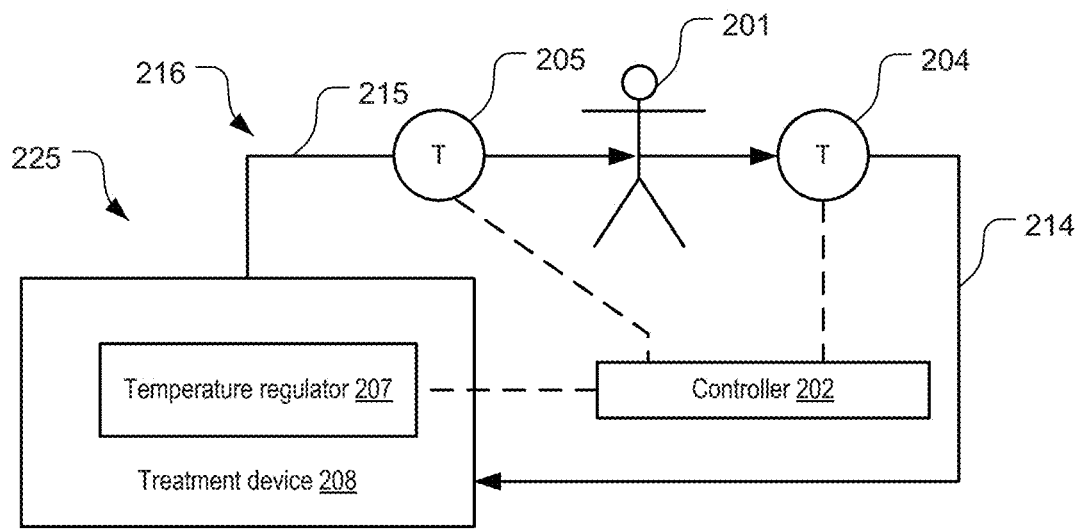
FIG. 9 illustrates an active temperature control mechanism for regulating body temperature of a subject based on the temperature of blood from the patient and optionally based on the temperature of the blood returned to the patient as well.
Figure 10:
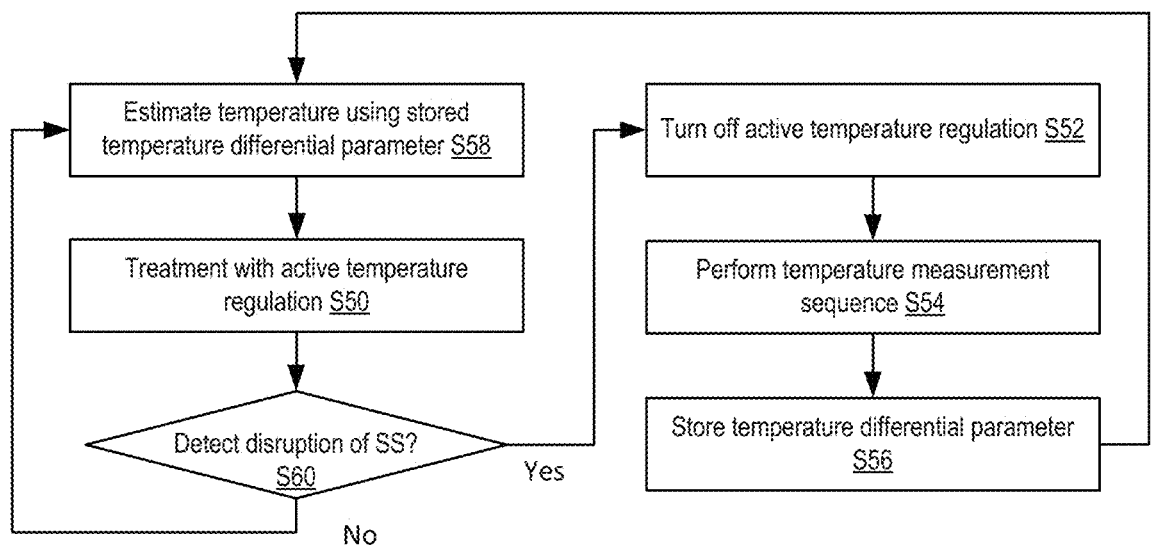
FIG. 10 illustrates a method of active temperature regulation using the disclosed temperature measurement embodiments.

FIG. 9 illustrates an active temperature control mechanism for regulating body temperature of a subject based on the temperature of blood from the patient and optionally based on the temperature of the blood returned to the patient 201 as well. A treatment system with a treatment device 208, a controller 202, and a temperature regulator 205. The system may be as described with reference to FIG. 5. The controller receives venous and arterial temperature signals from respective temperature sensors 205 and 204. The temperature sensors 205 and 204 are configured to indicate the temperature of blood in venous 215 and arterial 214 lines of a blood circuit 216 and to perform feedback control of the temperature regulator (e.g., a dialysate heater or heater/cooler, for example) to regulate the patient's 201 body temperature during a treatment. FIG. 10 illustrates a method of active temperature regulation using the disclosed temperature measurement embodiments in the system of FIG. 9 feedback control using the temperature indicated by sensor 205, 204 or a combination thereof. As discussed above and here, the core temperature is estimated to compensate for heat loss in the blood circuit connecting the patient and the temperature sensor and used as a control variable. The temperature difference between the core temperature as calculated using the disclosed embodiments and the temperature indicated by the temperature sensor 204 can be stored and used to estimate the core temperature after the temperature measurement at the multiple flow rates is performed, for example after the temperature measurement phase of the startup procedure. The temperature drop (or rise) may be store and applied as a fixed value DT which assumes that the net change in temperature remains constant.

$$Tp = DT + Tci \quad (5)$$

Instead, the LMTD can be calculated from the temperature measurement procedure and used with the estimated ambient temperature $T_a$ and the temperature from the sensor 204, $T_c$, to calculate a lump parameter X $$X = \frac{UA}{Q\rho c_p} = \frac{Q}{LMTD}(T_p - T_c) \quad (6)$$

where A is the heat transfer area of the blood circuit between the patient and the temperature sensor, Q is the volume flow rate of blood (here, at the time of calculating X), $T_c$ can be either $T_{c1}$ or $T_{c2}$, and the other parameters are as defined above. $T_p$ can be calculated from equation 7 based on the current temperature $T_c$ from sensor 204.

$$T_p = T_c + X\frac{LMTD}{F} \quad (7)$$

Where LMTD is calculated from equation 3e based on a current temperature $T_c$, estimated ambient temperature, and a current flow rate F. As should be clear from the current description, other temperature difference parameters may also be used rather than LMTD. For example, a constant average blood temperature of the blood circuit may be assumed rather than an exponentially changing temperature as assumed in using LMTD. Thus, the core temperature may be calculated at S54 and a temperature differential or parameter such as X (equation 6) may be derived and stored at S56 and thereafter used to calculate the core temperature at S58. At S50, the system 205 treats a patient 201 while regulating the venous temperature responsively to the temperature 204 using a final negative feedback control of the temperature regulator 207 targeting a set-point of a return temperature indicated by 205, where the set-point is the controlled variable of the outer negative feedback control based on the core temperature. Meanwhile the temperature indicated by sensor 204 is monitored and if a temperature vs time profile occurs that indicates that the heat transfer characteristic of the arterial line 214 between the sensor 204 has changed (disruption of steady state, "SS"), then at S60, the active temperature regulation may be halted and the core temperature acquired again according to the methods and devices described herein. Note that S60 may form a separate thread that interrupts a loop going from S50 to S58 rather than as illustrated so that the temperature is monitored for a heat transfer characteristic change continuously or at least frequently. The indication of a disruption of steady state may be indicated by a rate of change of temperature that is high enough to make it unlikely to be due to a change in the patient's body temperature. Mechanical disturbance of the blood circuit may be detected, for example by an accelerometer tension sensor connected between the blood processing system supporting the temperature sensor and the arterial portion of the blood circuit. Or the accelerometer may be on the blood circuit. These and other means may be provided to detect and indicate a disturbance or mechanical movement of the blood circuit. Other inputs such as video feed of the patient may be used to determine if there is a possible disruption. For example, a video of the patient which shows the patient shifting body position may indicate a significant change such as the arterial line being moved or covered by the patient's body.

The above methods rely on an estimate for the ambient temperature. The precise ambient temperature may not be known and the heat transfer environment of the blood circuit may not correspond well to a single measure of ambient temperature. For example, for a long arterial line connected between a treatment machine and a patient, parts of the line may be lying on a bed which is slightly warmer than the room temperature, parts of the room may be cooler than other parts due to drafts or even the presence of occupants in the room. An effective ambient temperature may produce greater accuracy. To estimate this additional unknown, the Tc for another flow rate $F_3$ may be used. Initially the estimate of ambient temperature $T_a$ is used to calculate an estimate for X according to equation 6 using $T_{c1}$ and $F_1$ or $F_2$ and $T_{c2}$. The latter, rearranged to place $T_a$ in terms of X calculated from LMTD using the core temperature measurement based on $T_{c3}$ and $F_3$, is:

$$T_a = \frac{T_{c3}e^{\frac{X}{F_3}} - T_p}{e^{\frac{X}{F_3}} - 1} \tag{8}$$

This value can be used for each iteration to update the estimate of $T_p$, then to update X and then to calculate a new $T_a$ and so on until the values of $T_a$ and $T_p$ converge.

Figure 11A:
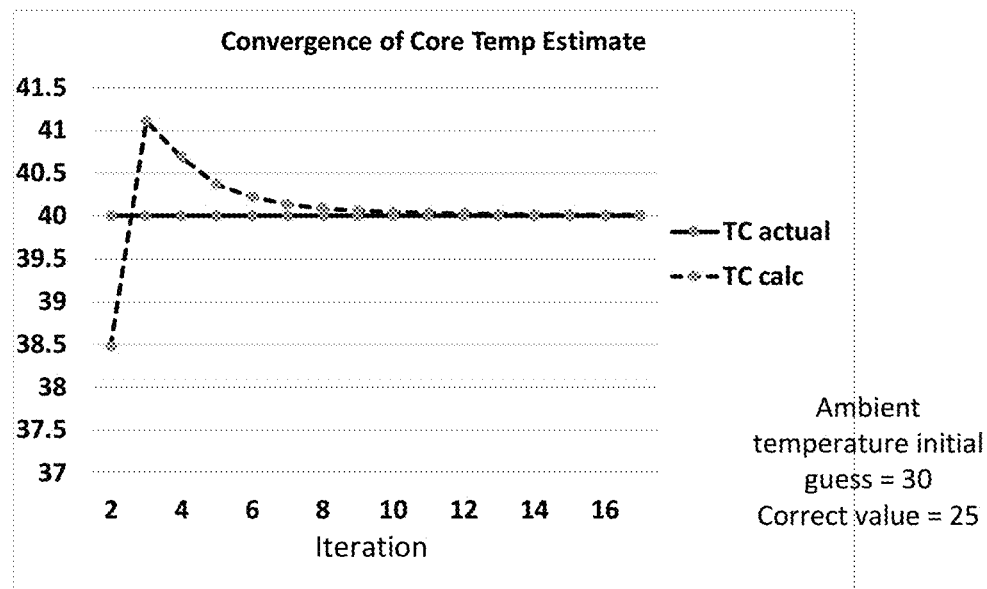
FIGS. 11A and 11B show results of simulations of a refined method based on that of FIGS. 3C and 3D which increase accuracy by optimizing an estimate of the temperature of the environment around a blood circuit.
Figure 11B:
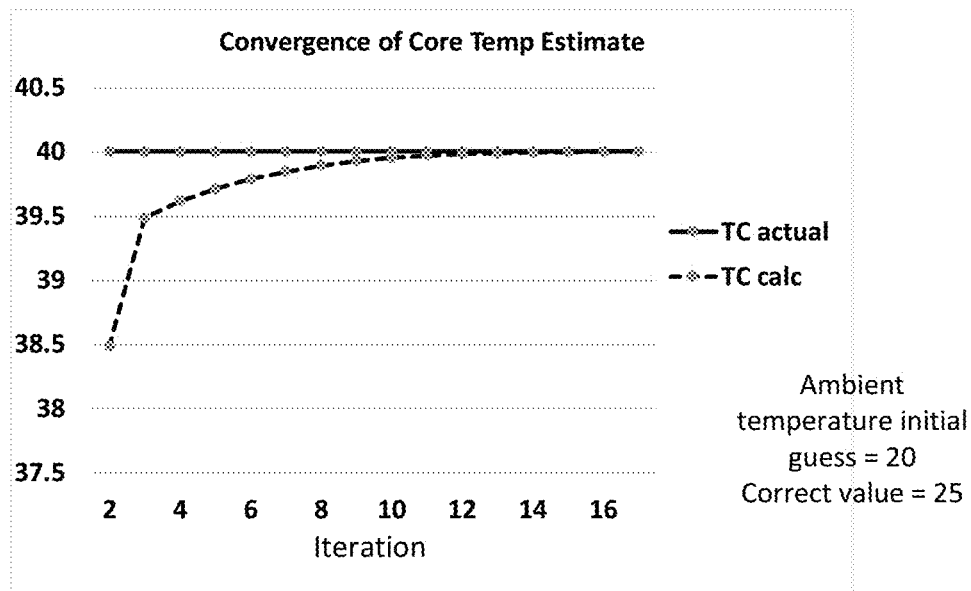
Figure 12A:
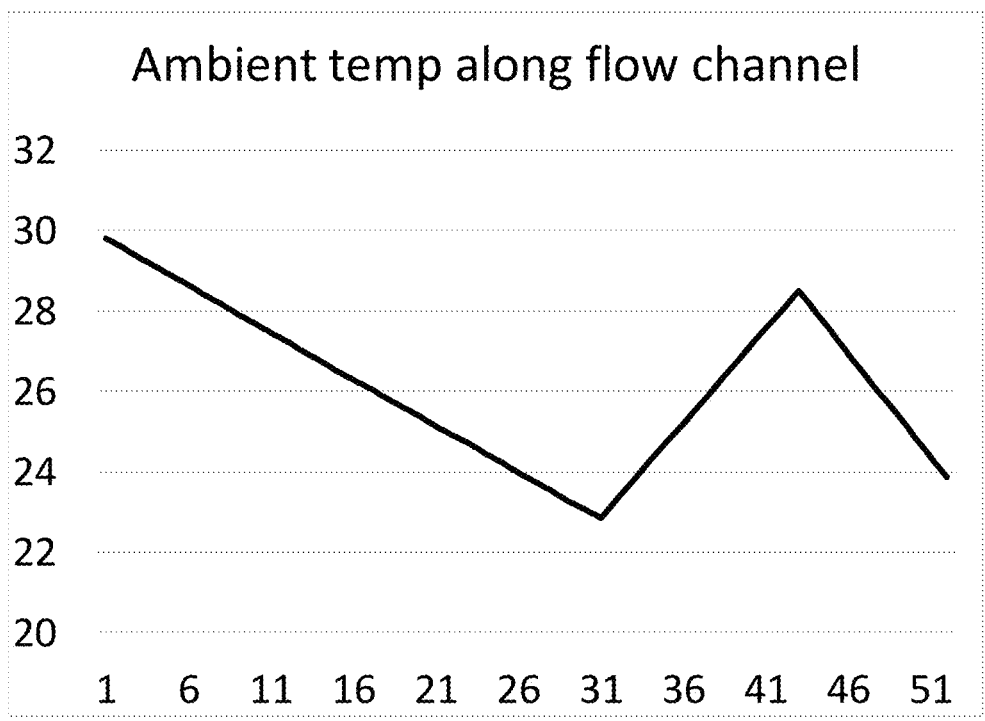
FIG. 12A shows an example of a variable environment temperature versus length to describe features of the temperature determination embodiments.
Figure 12B:
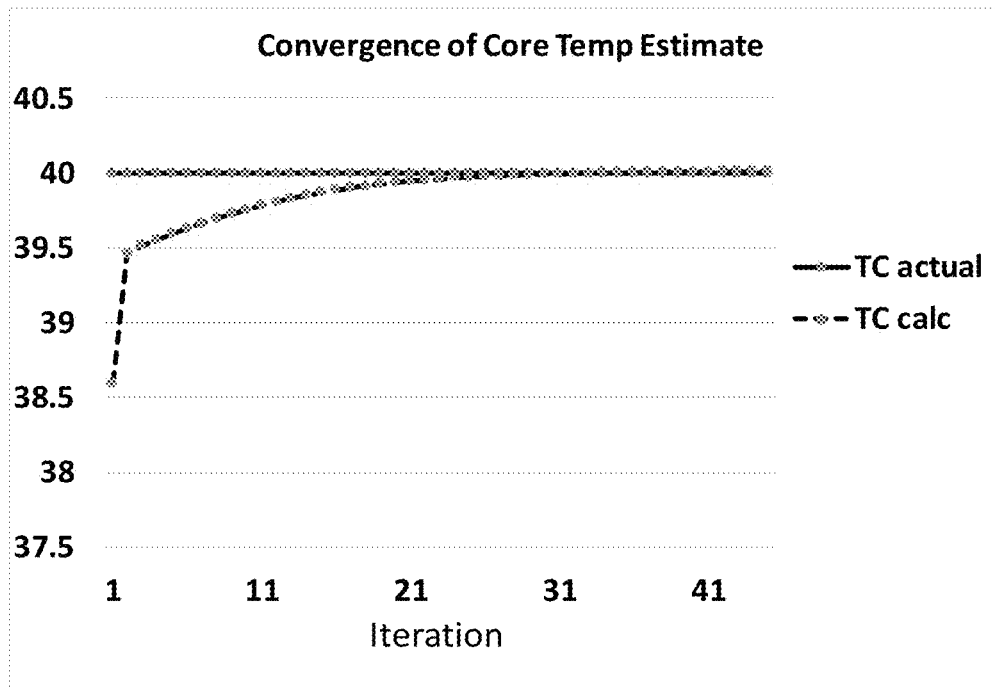
FIG. 12B shows the convergence of the core temperature estimate based on the profile of FIG. 12A.

FIGS. 11A and 11B show how $T_p$ converges using initial estimates of $T_a$ of 30 and 20, respectively with a correct constant value of 25. To test the situation where $T_a$ varies along the length of the blood channel between the patient and the temperature sensor, a varying $T_a$ was used to generate the simulation as shown in FIG. 12A. A model was generated that varied the simulated temperature surrounding a simulated fluid channel around ±10. This tested the calculation of an effective ambient temperature by iteration as described. The average value of $T_a$ along the length was 26.1. The value of $T_a$ after convergence using the procedure outlined above was 25.5. Tests of various profiles that $T_p$ converged to the correct value even for a variety of temperature variation profiles of the ambient temperature along the length of the blood circuit. FIG. 12B shows the convergence of the core temperature estimate based on the profile of FIG. 12A.

Figure 13:
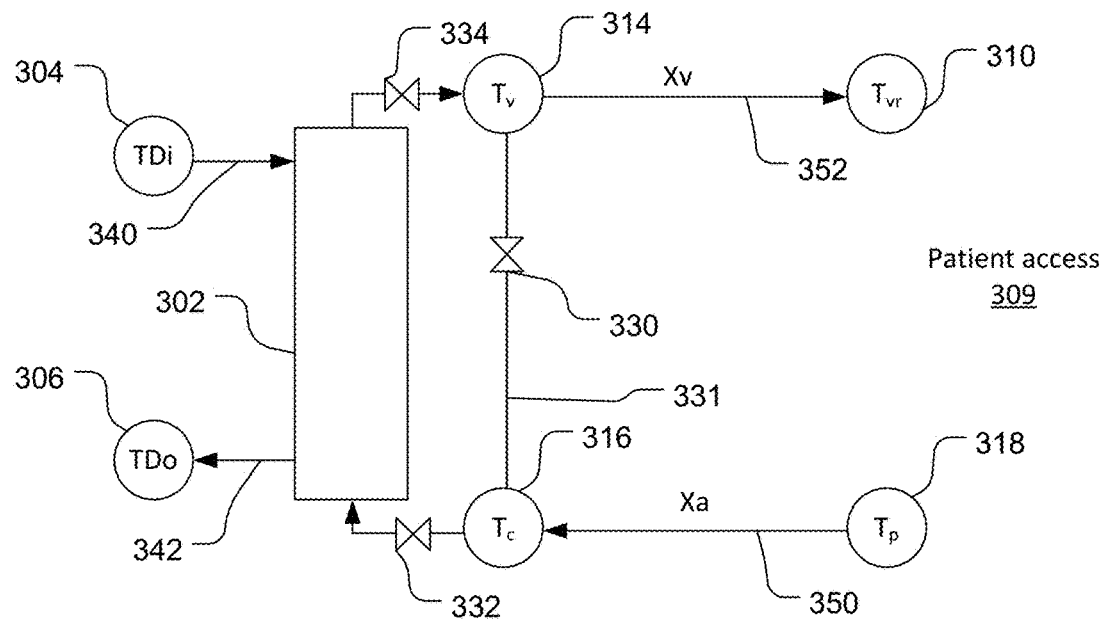
FIG. 13 shows a schematic of a dialysis system with various optional components for measuring temperature.

FIG. 13 shows a schematic of a dialysis system with various optional components for measuring temperature. A dialyzer 302 receives dialysate at a temperature $TD_i$ indicated by temperature sensor 304 from a dialysate supply line 340. The temperature of the dialyzer is indicated as TD. Spent dialysate emerges through a dialysate outlet 432 at a temperature $TD_o$ indicated by a temperature sensor 306. Blood enters the filter from a patient access 309 and flows through an arterial line 350. Blood initially enters at a temperature $T_p$ which may be indicated by a temperature sensor proximate the patient 318 but is, according to the disclosed embodiments calculated from a temperature Tc located remote from the patient access and indicated by a sensor 316. Heat exchanged with the external environment by the arterial line 350 occurs at a rate which may be represented by a lump parameter $X_a$. The temperature sensor 316 may be located at a treatment machine (not shown except for the components illustrated) measures temperature $T_c$ of blood flowing to the dialyzer 302 from the patient access 309. Blood enters the dialyzers 302 through a valve 332 (optional) and exits the filter through a valve 334 (optional). The temperature of blood exiting the filter and entering the venous line $T_v$ is indicated by temperature sensor 314. Blood flows through a venous line 352 and enters the patient access 309 at a temperature $T_{vr}$ indicated by temperature sensor 310. Heat from the venous line is transferred at a rate according to a lump parameter represented as $X_v$. An optional bypass branch 331 may be used to circulate blood from the arterial line 350 to the venous line 352 without passing through the dialyzer 302. This may be accomplished by opening valve 330 and closing valves 332 and 334.

Any of the foregoing components, including temperature sensors and valves may be omitted depending on the embodiment. Also, treatment devices other than dialyzers may be employed, for example it may be replaced with a hemofilter and replacement fluid line.

FIGS. 14A-14C show sets of control conditions for measuring core temperature using the embodiments of FIG. 13 according to respective embodiments. Each of these figures illustrates a configuration of FIG. 13 for implementing any of the embodiments where the patient temperature Tp is estimated using the disclosed embodiments where multiple blood flow rates are established and for each, at least one temperature measurement Tfi is made to calculate Tp.

Referring now to FIG. 14A, as described above, the dialysate flow may be halted after controlling the temperature of the dialysate in the dialyzer to a normal body temperature. Then blood may be passed through the dialyzer 302 without its temperature being continuously changed by the inflow of fresh dialysate at temperature TDi. As indicated above, this allows the blood temperature to be minimally modified by thermal contact with dialysate which is held stationary and initialized at normal body temperature. At any point during a treatment, a temperature measurement cycle may be started wherein the dialyzer temperature is brought to a normal body temperature or other predefined temperature and a cycle completed according to the above description of the measurement phase of the startup mode, i.e., blood is pumped at two flow rates and $T_{fi}$ is measured at each after establishment of steady state.

Referring to FIG. 14B, the controller of a temperature regulator that controls TDi is regulated for closed loop control to cause $T_v$ to be equal to $T_p$, where the latter is calculated using the methods disclosed where blood is pumped at different flow rates and the patient temperature is estimated. The estimation of $T_p$ may be done using any of the methods described. Once $T_p$ is established, it is used to estimate $X_a$ using equation 6. $X_v$ may be assumed to be the same at $X_a$ or approximated responsively to $X_a$. For example, if $X_v$ is a longer or shorter tube than $X_a$ and both are in the same ambient space, $X_v$ can be scaled according to the difference in length according to known principles of heat transfer calculations. Then during a temperature measurement cycle, the $T_v$ is calculated from $T_{fo}$ based on $X_v$ and an adjusted $T_{fo}$ (Tv-calculated) is actively controlled to be equal to $T_a$ while the blood flow rate is adjusted to the two flow rates required to obtain a steady state temperature reading from $T_{fi}$ from which the patient core temperature $T_p$ can be calculated using the disclosed methods.

Figure 14D:
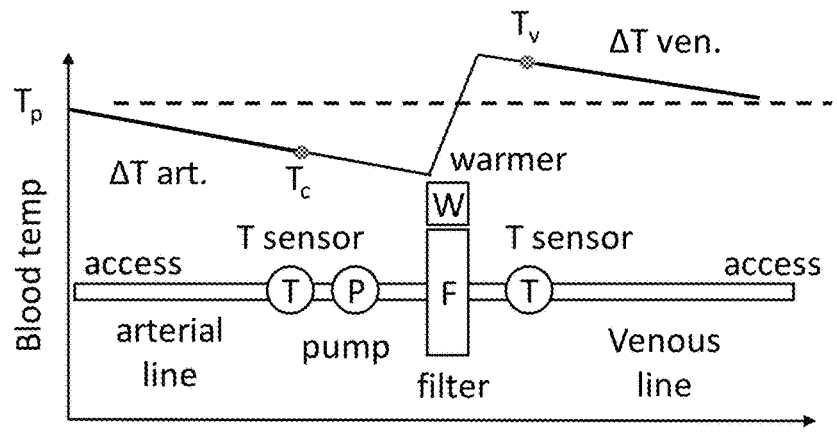
FIG. 14D represents adiabatic regulation for return blood temperature identical to patient blood temperature as measured according to the embodiments.

Referring to FIG. 14D, the blood temperature is figuratively plotted versus position along the length of the blood circuit. The temperature falls as it flows through the arterial line up to the temperature sensor that measures $T_c$. Then the blood temperature continues to fall until it warmed by contact with heated fluid in the dialyzer (filter F). The temperature of the blood is increased to a peak temperature whereupon it falls again until it is returned. A temperature sensor for the venous line measures temperature $T_v$, which is the temperature of the blood before it begins flowing through the venous line. This temperature $T_v$ is the control target. The control goal in embodiment of FIG. 14B is to regulate $T_v$ such that the final return temperature is the same as $T_p$, calculated by the system. The assumption that allows this to be done is that the external temperature and thermal resistance of the arterial line and the venous lines are the same.

For simplicity, $T_v$ may be calculated based on the assumption that the blood temperature in the venous and arterial lines is each uniform along its length. The ratio of the changes in blood temperature in the venous ($T_v-T_p$) and arterial ($T_p-T_c$) lines is the same as the ratio of the differences between the average blood temperature in the arterial ($T_{ba}$) and venous ($T_{bv}$) lines from the ambient temperature:

$$\frac{T_{bv} - T_a}{T_{ba} - T_a} = \frac{T_p - T_a + T_v - T_a}{T_p - T_a + T_C - T_a} = \frac{T_v - T_p}{T_p - T_c} \quad (9)$$

Then, solving for $T_v$ $$T_v = \frac{2T_aT_p - T_aT_c - T_p^2}{T_a - T_c} \quad (10)$$

Note that the configuration of FIG. 14B may be used for active temperature control. That is, $T_v$ can be compensated for heat loss to obtain a high accuracy estimate for $T_{vr}$ indicated at 310, which may then be controlled by controlling the temperature regulator for the dialysate (i.e., the heater, cooler, or heater/cooler that determines $TD_i$) in closed loop fashion. Also note that in additional embodiments, instead of calculating $T_v$ according to equation 10, $T_v$ may be taken simply as $T_c-T_a$ for the current operating conditions. This estimate would apply where the $T_p-T_c$ is much greater than $T_b-T_a$. That is the change in the blood temperature (average blood temperature in arterial or venous line being indicated by $T_b$) is much less than the difference between blood temperature and ambient such that the rate of heat loss in the venous and arterial lines is approximately the same.

Because the calculation of $T_p$ may require the change of blood flow to multiple different flow rates in order to acquire $T_{c1}$ and $T_{c2}$ or $T_{c1}$, $T_{c2}$, and $T_{c3}$ or other variations (more flow rates could be done for super-sampling in order to reduce error), any error in the calculated value of $T_p$ may result in a net effect on the patient's body temperature. For example, the blood may be returned warmer or cooler than it emerged from the patient resulting in a net heat addition or removal from the patient. To avoid this problem, the patient core temperature may be calculated, including the acquisition of $T_{c1}$ and $T_{c2}$ or $T_{c1}$, $T_{c2}$, and $T_{c3}$ at the respective flow rates, repeatedly so as to cause the patient's body temperature to converge on its natural (either afebrile or febrile) body temperature. This may permit more accurate diagnosis of abnormal body temperature and associated conditions.

Referring to FIG. 14C, for a bypass flow is established by closing valves 332 and 334 and opening valve 330. Blood flows from the arterial line 350 back to the patient through venous line 352 bypassing the dialyzer 302. This prevents the transfer of heat between the dialysate and the blood thereby preventing the dialysate from affecting the temperature measurement. The effect is similar to the embodiment of FIG. 14A except that the blood temperature is not affect by any difference in the dialysate temperature in the dialyzer 302 and the temperature of the blood passing through it.

Note that although the target temperature of the above system is identified as core, it is understood that the patient access may be located in a peripheral part of the that has a natural normal temperature that is lower than the patient core temperature. For example, a fistula in the arm of a patient may deliver blood at a lower than the core temperature of a patient. In every instance where the term core is used, it may be replaced by a suitable term to reflect the alternative and thus the term is not considered limiting of the disclosed subject matter.

The above methods may be modified such that the controller outputs to a user interface an instruction to cause the patient to remain still and to maintain steady thermal conditions in the room during temperature measurements. The procedure may include an output of an instruction and a delay until an acknowledgement is indicated by an operator to proceed with temperature measurement. This may help to ensure that steady state conditions are established prior to the temperature measurement process (e.g., S40-S48). For example, this operation may be inserted between S38 and S40 in FIG. 8.

Since there is no flow in the treatment fluid compartment and the temperature of the treatment fluid compartment is initialized to a normal body temperature level, the flow in the treatment fluid circuit is substantially adiabatic.

Figure 7:
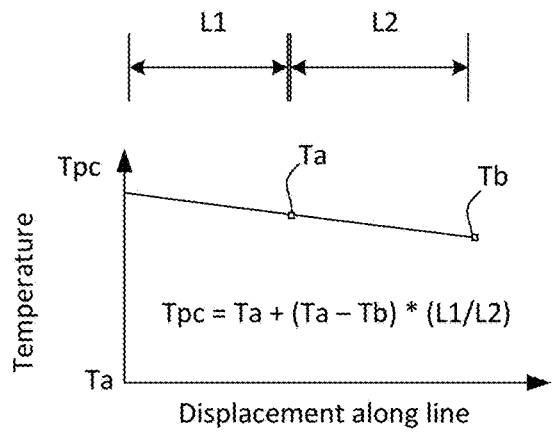
FIG. 7 shows a graph of blood temperature versus displacement of blood along a flow channel, according to embodiments of the disclosed subject matter.

In the embodiments disclosed above, temperature readings are obtained for multiple flow rates to enable the solution of a thermal model but fitting a function to it. In embodiments, multiple temperature readings at different positions along the length of a tube can be obtained to permit the core temperature to be extrapolated. For example, referring to FIG. 7, a temperature $T_a$ is sampled at a position $L_1$ distance from a patient access and a temperature $T_b$ is sampled at a position $L_2$ distance from the patient access. In a linear model where the temperature change is small compared to the temperature difference between the fluid and the ambient, the core temperature $T_p$ can be obtained from $T_p=T_a+(T_a-T_b)*(L_1/L_2)$.

The below disclosure provides an embodiment that uses an average temperature difference of the blood line.

$T_p$=patient temperature (° C.)
$T_c$=sensor temperature (° C.)
$T_b$=(Tb+Tc)/2 (° C.)
$T_a$=ambient temperature (° C.)
F=Mass Flow (gm/sec.)
$F_1$=first flow rate; $F_2$=second flow rate
$c_p$=specific heat (Joules/(gm ° C.))=3.78 J/gm ° C.
P=heat transfer rate (W)
Θ=thermal resistance (° C./W)

This model makes the following simplifying assumptions:
1. The blood temperature changes linearly in the line from the patient to the measurement point which is linear. The blood temperature is represented as the average of the patient temperature ($T_p$) and the temperature measured at the sensor ($T_c$).

$T_b=(T_p+T_c)/2$

2. The heat transfer rate (power units) from the blood line to the ambient is given by the difference between the average blood temperature and the ambient temperature divided by the thermal resistance Θ.

$P=(T_b-T_a)/Θ$

3. The thermal conditions are steady. Specifically, the patient temperature and the blood heat capacity are constant during a measurement.

$T_p-T_a$ (the temperature change in the blood between the patient and the sensor) is related to the heat transfer rate, mass flow rate, and heat capacity of the blood.

Heat Capacity Equation for Steady State Flow $$P = (T_p - T_c) F c_p$$

Patient Temperature Calculation:

Assume P is constant for 2 mass flows rates $F_1$, $F_2$ and calculate an estimate for Tp. This assumption has a minor inaccuracy because Tb is different for $F_1$ and $F_2$.

$$T_p = \frac{(T_{c1}F_1) - (T_{c2}F_2)}{F_1 - F_2}$$

Choice of $F_1$ and $F_2$:

$F_1$ may be chosen as the maximum safe blood flow because high mass flow reduces the temperature change along the blood line.

$F_2$ may be chosen to maximize the accuracy of the patient temperature determination. A relatively low $F_2$ results in higher accuracy of measured temperature difference from $F_1$ and higher accuracy of flow control difference from $F_1$ which improve the accuracy of the calculation. A relatively high $F_2$ reduces the change in Tb between the measurements which reduces the error due to the assumption that the heat loss power is the same for both flow rates. A temperature measurement and flow control tolerance analysis along with an analysis of the effect of different ambient temperatures can be used to determine the optimal ratio of $F_1$ to $F_2$. Rather than using a fixed ratio of $F_1$ to $F_2$, in embodiments, the ratio may be adjusted to provide a fixed difference in Tb between $F_1$ and $F_2$.

The foregoing embodiments may be modified by compensating for the change in heat loss power due to the change in the difference between $T_b$ and $T_a$ at $F_2$. The ambient temperature ($T_a$) can be measured or otherwise estimated. The approach is as described above with reference to equations 3b and 3c and more generally according to equation 3a, supra. Note that in a variation, instead of deriving $T_p$ as indicated, an estimate or initial guess can be used instead because the improvement process described below and elsewhere will converge to an optimum of $T_p$.

Estimate $T_a$

Calculate $T_{b1}$ for $F_1$:

$$T_{b1} = (T_p + T_{c1})/2$$

Calculate $T_{b2}$ for $F_2$ $$T_{b2} = (T_p + T_{c2})/2$$

Calculate the heat loss to ambient power ratio (Pr) for $F_1$ to $F_2$:

$$Pr = (T_{b1} - T_a)/(T_{b2} - T_a)$$

Calculate the ambient corrected patient temperature:

$$T_p^* = \frac{(T_{c1}F_1) - (PrT_{c2}F_2)}{F_1 - (PrF_2)}$$

This process can be iterated till the new value of $T_p$ converges on a final value.

Figure 15C:
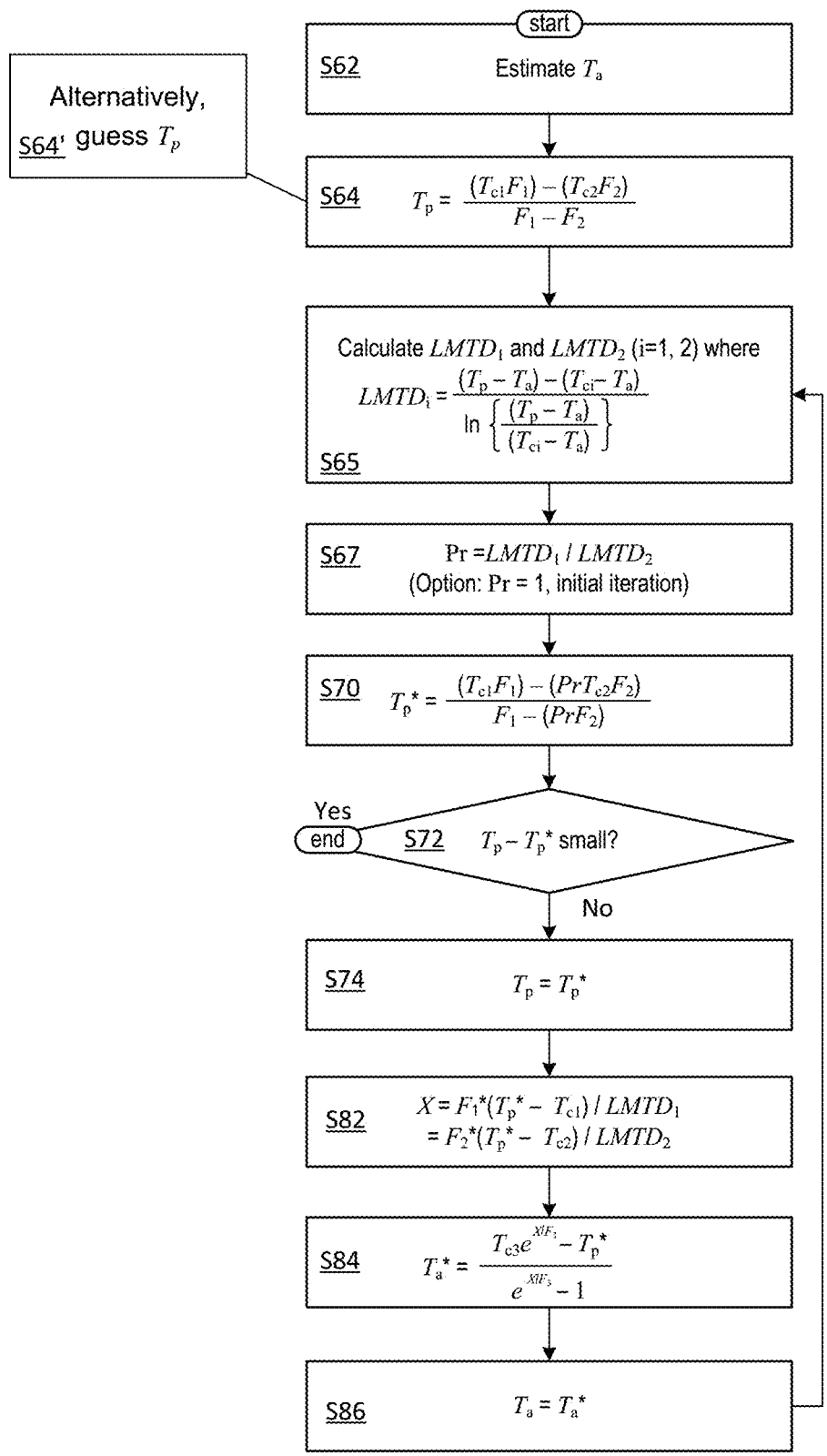
Figure 16A:
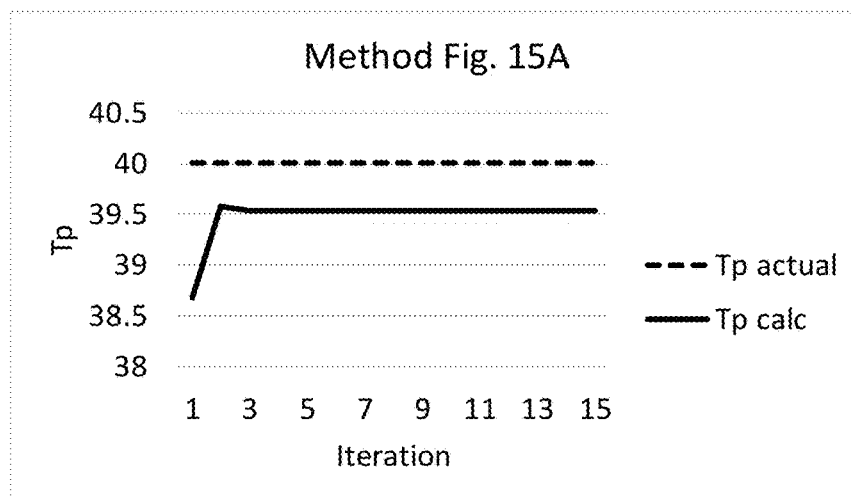
FIGS. 16A through 16C show simulations corresponding to the methods of FIGS. 15A through 15C.

FIGS. 15A through 15C illustrate the some of the embodiments discussed above for calculating $T_p$ in a format that highlights their similarities and differences. Referring to FIG. 15A, an estimate, measurement, or guess for the ambient temperature is made at S62. Then the patient core temperature $T_p$ is calculated as discussed above at S64. The average blood temperatures corresponding to each of the blood flow rates are calculated at A66. A ratio of the heat transfer rates for the two flow rates is calculated at S68 using the ambient temperature (guess, estimate, or measurement) and the average blood temperatures. The heat transfer rate is used to calculate a revised estimate of the patient core temperature $T_p^*$ at S70. At S72 a termination condition is calculated and if $T_p$ is deemed to have converged, execution ends but if not, the revised core temperature $T_p^*$ is used in S66 and steps S66 to S70 repeated until the termination condition is satisfied. In the example, a difference between the current and revised $T_p^*$ below a threshold is used to determined convergence of $T_p$. A result of an example calculation using this method is shown in FIG. 16A for one set of simulated conditions.

Figure 16B:
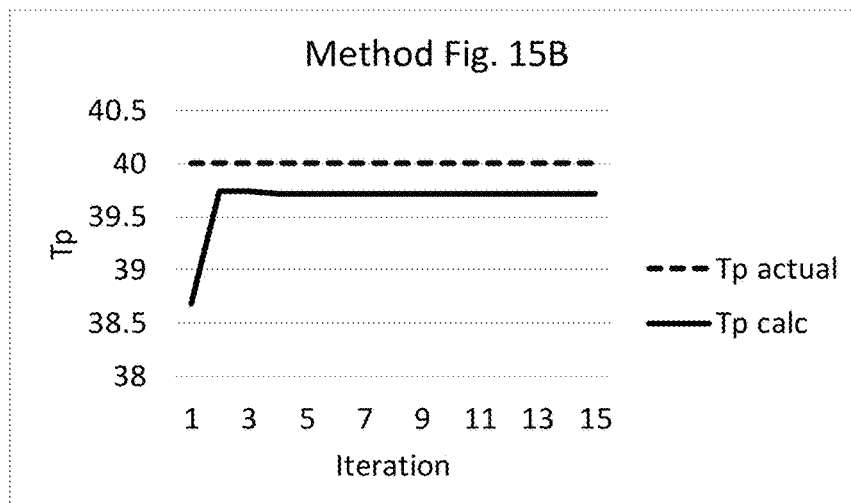

Referring now to FIG. 15B, the iterative process is the same as in FIG. 15A except that instead of using an average temperature difference to calculate the heat transfer rate ratio at S68, a ratio of log mean temperature difference (LMTD) is calculated at S67, instead. The latter is calculated at S65 from ambient temperature, the initial $T_p$, and the measured temperatures corresponding to the two flow rates. A result of an example calculation using this method is shown in FIG. 16B for the same set of simulated conditions as for FIG. 16A.

Figure 16C:
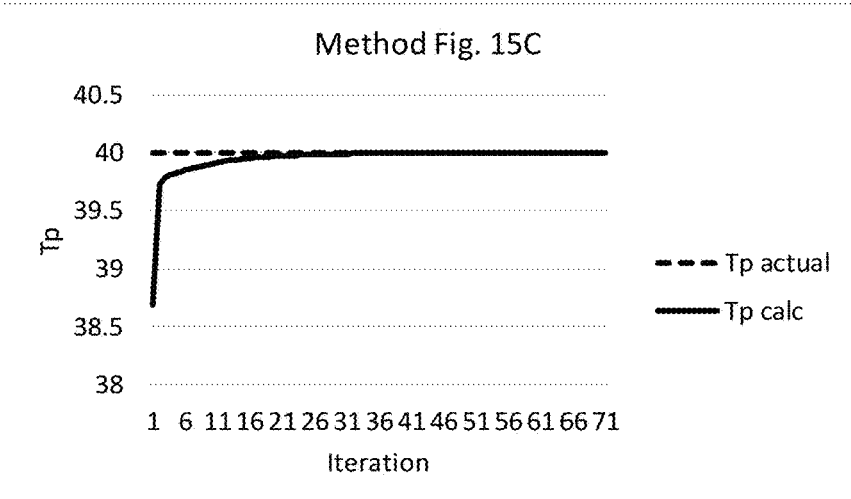

Referring now to FIG. 15C, the iterative process is as in FIG. 15B except that the ambient temperature guess, estimate, or measurement is iteratively updated S82 to S86 before returning to S65 and after S74. The update of ambient temperature relies on an additional data point, namely, a third flow rate $F_3$ and a corresponding temperature $T_{c3}$ where the third flow rate is different from the other two, $F_1$ and $F_2$. At S82, equation 6 is used with the first or second flow conditions to calculate lump parameter X. At S84, the lump parameter X is then plugged into equation 8 with the third flow rate $F_3$ and a corresponding temperature $T_{c3}$ to calculate a revised ambient temperature. The ambient temperature is set to the new value at S86 and the iterative process repeated until the termination condition is satisfied. A result of an example calculation using this method is shown in FIG. 16C for the same set of simulated conditions as for FIGS. 16A and 16B. Note that FIG. 15C process takes many more iterations but converges to a more accurate estimate of the patient core temperature $T_p$. Note that a variant of the method of FIG. 15C, an average temperature difference may be calculated instead of LMTD similar to the method of FIG. 15A. Then X can be calculated accordingly using a modified equation 6 that replaces LMTD with the average blood temperature $T_b$. Then $T_a$ can be obtained from equation 6 solved for $T_a$, namely:

$$T_a = T_b - (T_p - T_c)\frac{F}{X} \tag{9}$$

It will be evident that in the methods embodied in FIG. 15C and variants an effective temperature of the environment is calculated based on the assumption of a uniform temperature of the external environment of the blood circuit that agrees with the measured temperatures. That is, even where a temperature of the environment of the blood circuit varies, the models assume a constant external environment temperature and solve for it.

Note that FIGS. 15A-15C are not intended to be comprehensive. The method of FIG. 15C, for instance, may be modified to use the difference between an average blood and the external temperature. Note that ambient temperature and temperature of the external environment are used synonymously here. Note also that the true ambient temperature is independent of the effective external environment temperature calculated in certain embodiments.

The above methods may solve, in embodiments, for two parameters, namely a uniform heat transfer resistance and blood inlet temperature $T_p$ using two relationships defining the relationship between the temperature change in the flowing blood along the fluid circuit and the driving temperature difference between an estimated external environment temperature and a blood temperature inside the blood circuit. In embodiments, an additional unknown, the external environment temperature is solved for by adding a further relationship based on a third flow rate.

Note that temperatures of blood may be taken along any part of the blood circuit including the venous line as long as the calculation used for inferring the core temperature can take into account the heat transfer properties along the entire circuit up to the point of measurement. Also, any of the embodiments may be modified for the measurement of core temperature using any fluid drawn from the body of the subject at a controllable rate, which fluid is initially at an equilibrium temperature with the subject's core. Examples of other fluids are cerebrospinal fluid, urine, ultrafiltrate from an implantable artificial kidney, and spent peritoneal dialysate.

Note that in any of the embodiments, a finite-element dynamic model of a tube may be fitted to unsteady state temperature measurements, position along the tube, and time. Such a model may have multiple finite element nodes within the wall of the tube which has properties that may provide predefined thermal capacity and conductivity. The finite element model may be segmented along the length of the tube. An analytical model may also be employed which is unsteady.

According to embodiments, the disclosed subject matter includes a method of detecting a fever in a patient undergoing extracorporeal blood processing. The method includes controlling, using an automatic controller, a rate of flow of blood through a flow channel connecting a patient to a temperature sensor to establish a first flow rate. The method further includes, at the first flow rate, permitting the flow of an unknown quantity of heat to or from the flow channel connecting a patient to a temperature sensor. At the first flow rate, at least one temperature of the flow channel is measured using the temperature sensor and first temperature data recorded that is responsive to a result of the measuring. Next the method includes controlling, using the automatic controller, a rate of flow of blood through the first flow channel to establish a second flow rate, different from the first and repeating the permitting and measuring at the second flow rate and recording a second temperature data responsively to the corresponding measuring. The method may include calculating an inferred temperature from the first and second temperature data, the inferred temperature representing a temperature remote from the temperature sensor. The method may further include comparing the inferred temperature to data responsive to at least one reference temperature and outputting data to a user interface indicating data responsive to a result of the comparing.

To form additional embodiments, any method embodiment may be modified such that the establishing includes holding the respective first and second flow rates for a period of time effective to establish an unchanging temperature indicated by the temperature sensor. To form additional embodiments, any method embodiment may be modified such that the flow channel is an arterial line. To form additional embodiments, any method embodiment may be modified such that the controlling to establish a first flow rate and the controlling to establish a second flow rate include flowing at a respective rate for an interval effective to establish a steady state condition in terms of heat flow into or out of the fluid channel. To form additional embodiments, any method embodiment may be modified such that the flow channel is an arterial line. To form additional embodiments, any method embodiment may be modified such that the permitting includes permitting the flow of heat from the flow channel to the ambient environment through a blood carrying tube.

According to embodiments, the disclosed subject matter includes a method of detecting a fever in a patient undergoing extracorporeal blood processing. The method includes controlling, using an automatic controller, a rate of flow of blood through a flow channel connecting a patient to a temperature sensor to establish a first flow rate. The method includes, at the first flow rate, permitting the flow of an unknown quantity of heat to or from the flow channel connecting a patient to a temperature sensor. The method further includes, at the first flow rate, minimizing a flow of heat from or to the flow channel at the temperature sensor and while measuring at least one temperature of the flow channel using the temperature sensor, the minimizing including actively regulating a heat flux to minimize a heat flux from the flow channel through the temperature sensor. The method further includes recording a first temperature data responsively to the measuring and then controlling, using the automatic controller, a rate of flow of blood through the first flow channel to establish a second flow rate, different from the first. The method includes repeating the permitting, minimizing, and measuring at the second flow rate and recording a second temperature data responsively to the corresponding measuring and calculating an inferred temperature from the first and second temperature data, the inferred temperature representing a temperature remote from the temperature sensor. The method includes comparing the inferred temperature to data responsive to at least one reference temperature and outputting data to a user interface indicating data responsive to a result of the comparing.

To form additional embodiments, any method embodiment may be modified such that the establishing includes holding the respective first and second flow rates for a period of time effective to establish an unchanging temperature indicated by the temperature sensor. To form additional embodiments, any method embodiment may be modified such that the flow channel is an arterial line. To form additional embodiments, any method embodiment may be modified such that the controlling to establish a first flow rate and the controlling to establish a second flow rate include flowing at a respective rate for an interval effective to establish a steady state condition in terms of heat flow into or out of the fluid channel. To form additional embodiments, any method embodiment may be modified such that the flow channel is an arterial line. To form additional embodiments, any method embodiment may be modified such that the permitting includes permitting the flow of heat from the flow channel to the ambient environment through a blood carrying tube. To form additional embodiments, any method embodiment may be modified such that the data responsive to a condition includes data indicating that the patient has a fever.

According to embodiments, the disclosed subject matter includes a blood treatment system. A blood treatment machine has a programmable controller and at least a blood pump whose pumping rate is controlled by the controller. The blood treatment machine is arranged to receive a disposable blood circuit, the blood treatment machine having a temperature sensor positioned on the blood treatment machine to measure a temperature of blood flowing through an attached blood circuit. The controller is programmed to establish a flow of blood at a first rate according to a first predefined condition, whereupon the controller records first temperature data representing a temperature indicated by the temperature sensor. The controller is programmed subsequently to establish a flow of blood at a second rate according to a second predefined condition, whereupon the controller records second temperature data representing a temperature indicated by the temperature sensor. The controller is programmed to calculate patient temperature data indicating a temperature of the fluid circuit responsively to both the first and second temperature data. And to output a patient temperature signal to a user interface responsively to the patient temperature data.

To form additional embodiments, any system embodiment may be modified such that the patient temperature signal includes an indication that the patient has a fever. To form additional embodiments, any system embodiment may be modified to include the comparison by the controller of the patient temperature data to a predefined range. To form additional embodiments, any system embodiment may be modified such that the first predefined condition and the second predefined condition are time intervals. To form additional embodiments, any system embodiment may be modified such that the first predefined condition and the second predefined condition are identical time intervals. To form additional embodiments, any system embodiment may be modified such that the first predefined condition and the second predefined condition include a detected establishment of unchanging temperature indicated by the temperature sensor and determined by the controller. To form additional embodiments, any system embodiment may be modified such that the temperature sensor is a contact-type temperature sensor that has a surface temperature element that engages an outside of an attached blood circuit.

According to first embodiments, the disclosed subject matter includes a method of determining a core in a patient undergoing extracorporeal blood processing. The method includes controlling, using an automatic controller, a rate of flow of blood through a flow channel connecting a patient to a temperature sensor to establish a first flow rate. The method includes, at the first flow rate, permitting the flow of an unknown quantity of heat to or from the flow channel connecting a patient to a temperature sensor. The method includes, at the first flow rate, measuring at least one temperature of the flow channel using the temperature sensor. The method includes, recording a first temperature data responsively to said measuring. The method includes controlling, using the automatic controller, a rate of flow of blood through the first flow channel to establish a second flow rate, different from the first. The method includes repeating the permitting and measuring at the second flow rate and recording a second temperature data responsively to the corresponding measuring. The method includes calculating an extrapolated temperature from the first and second temperature data, the extrapolated temperature representing a temperature remote from the temperature sensor. The method includes comparing the extrapolated temperature to data responsive to at least one reference temperature and outputting data to a user interface indicating data responsive to a result of said comparing.

Variations of the first embodiments may be provided to form additional first embodiments in which the establishing includes holding the respective first and second flow rates for a period of time effective to establish an unchanging temperature indicated by said temperature sensor. Variations of the first embodiments may be provided to form additional first embodiments in which the flow channel is an arterial line. Variations of the first embodiments may be provided to form additional first embodiments in which said controlling to establish a first flow rate and said controlling to establish a second flow rate include flowing at a respective rate for an interval effective to establish a steady state condition in terms of heat flow into or out of the fluid channel. Variations of the first embodiments may be provided to form additional first embodiments in which the flow channel is an arterial line. Variations of the first embodiments may be provided to form additional first embodiments in which the permitting includes permitting the flow of heat from the flow channel to the ambient environment through a blood carrying tube.

Variations of the first embodiments may be provided to form additional first embodiments in which the data responsive to a condition includes data indicating that the patient has a fever.

Variations of the first embodiments may be provided to form additional first embodiments in which the method further includes regulating a patient core temperature by adding or removing heat from the patient and/or patient's blood responsively to a result of the calculating. Variations of the first embodiments may be provided to form additional first embodiments in which the controller is further programmed to regulate the patient core temperature responsively to the calculated patient temperature. Variations of the first embodiments may be provided to form additional first embodiments in which the method further includes regulating a patient core temperature by adding or removing heat from the patient and/or patient's blood responsively to a result of the calculating, wherein the adding or removing is indicated by a predefined therapeutic treatment modality. Variations of the first embodiments may be provided to form additional first embodiments in which the method further includes regulating a patient core temperature by adding or removing heat from the patient and/or patient's blood responsively to a result of the calculating, wherein the adding or removing is indicated by a predefined cardiac therapeutic treatment modality. Variations of the first embodiments may be provided to form additional first embodiments in which the method further includes regulating a patient core temperature by adding or removing heat from the patient and/or patient's blood responsively to a result of the calculating, wherein the adding or removing is indicated by a predefined brain therapeutic treatment modality.

Variations of the first embodiments may be provided to form additional first embodiments in which the data is responsive to a condition includes data indicating that the patient has a fever.

According to second embodiments, the disclosed subject matter includes a method of detecting a fever in a patient undergoing extracorporeal blood processing. The method includes controlling, using an automatic controller, a rate of flow of blood through a flow channel connecting a patient to a temperature sensor to establish a first flow rate. The method includes, at the first flow rate, permitting the flow of an unknown quantity of heat to or from the flow channel connecting a patient to a temperature sensor. The method includes, at the first flow rate, minimizing a flow of heat from or to the flow channel at the temperature sensor and while measuring at least one temperature of the flow channel using the temperature sensor, the minimizing including actively regulating a heat flux to minimize a heat flux from the flow channel through the temperature sensor. The method includes recording a first temperature data responsively to said measuring. The method includes controlling, using the automatic controller, a rate of flow of blood through the first flow channel to establish a second flow rate, different from the first. The method includes repeating the permitting, minimizing, and measuring at the second flow rate and recording a second temperature data responsively to the corresponding measuring. The method includes calculating an extrapolated temperature from the first and second temperature data, the extrapolated temperature representing a temperature remote from the temperature sensor. The method includes comparing the extrapolated temperature to data responsive to at least one reference temperature and outputting data to a user interface indicating data responsive to a result of said comparing.

Variations of the second embodiments may be provided to form additional second embodiments in which the establishing includes holding the respective first and second flow rates for a period of time effective to establish an unchanging temperature indicated by said temperature sensor. Variations of the second embodiments may be provided to form additional second embodiments in which the flow channel is an arterial line. Variations of the second embodiments may be provided to form additional second embodiments in which said controlling to establish a first flow rate and said controlling to establish a second flow rate include flowing at a respective rate for an interval effective to establish a steady state condition in terms of heat flow into or out of the fluid channel. Variations of the second embodiments may be provided to form additional second embodiments in which the flow channel is an arterial line. Variations of the second embodiments may be provided to form additional second embodiments in which the permitting includes permitting the flow of heat from the flow channel to the ambient environment through a blood carrying tube. Variations of the second embodiments may be provided to form additional second embodiments in which the data responsive to a condition includes data indicating that the patient has a fever.

Variations of the second embodiments may be provided to form additional second embodiments in which the method further includes regulating a patient core temperature by adding or removing heat from the patient and/or patient's blood responsively to a result of the calculating. Variations of the second embodiments may be provided to form additional second embodiments in which the method further includes regulating a patient core temperature by adding or removing heat from the patient and/or patient's blood responsively to a result of the calculating. Variations of the second embodiments may be provided to form additional second embodiments in which the method further includes regulating a patient core temperature by adding or removing heat from the patient and/or patient's blood responsively to a result of the calculating, wherein the adding or removing is indicated by a predefined therapeutic treatment modality. Variations of the second embodiments may be provided to form additional second embodiments in which the method further includes regulating a patient core temperature by adding or removing heat from the patient and/or patient's blood responsively to a result of the calculating, wherein the adding or removing is indicated by a predefined cardiac therapeutic treatment modality. Variations of the second embodiments may be provided to form additional second embodiments in which the method further includes regulating a patient core temperature by adding or removing heat from the patient and/or patient's blood responsively to a result of the calculating, wherein the adding or removing is indicated by a predefined brain therapeutic treatment modality.

Variations of the second embodiments may be provided to form additional second embodiments in which the data is responsive to a condition includes data indicating that the patient has a fever.

According to third embodiments, the disclosed subject matter includes a blood treatment system that includes a blood treatment machine. The blood treatment machine has a programmable controller and at least a blood pump whose pumping rate is controlled by the controller. The blood treatment machine is arranged to receive a disposable blood circuit. The blood treatment machine has a temperature sensor positioned on the blood treatment machine to measure a temperature of blood flowing through an attached blood circuit. The controller is programmed to establish a flow of blood at a first rate according to a first predefined condition, whereupon the controller records first temperature data representing a temperature indicated by said temperature sensor. The controller is programmed subsequently to establish a flow of blood at a second rate according to a second predefined condition, whereupon the controller records second temperature data representing a temperature indicated by said temperature sensor. The controller is further programmed to calculate patient temperature data indicating a core patient temperature responsively to both said first and second temperature data. The controller is further programmed to output a patient temperature signal to a user interface responsively to said patient temperature data.

Variations of the third embodiments may be provided to form additional third embodiments in which the patient temperature signal includes an indication that the patient has a fever. Variations of the third embodiments may be provided to form additional third embodiments in which the controller compares the patient temperature data to a predefined range and said patient temperature signal is responsive to a result of such a comparison. Variations of the third embodiments may be provided to form additional third embodiments in which the first predefined condition and the second predefined condition are time intervals. Variations of the third embodiments may be provided to form additional third embodiments in which the first predefined condition and the second predefined condition are identical time intervals. Variations of the third embodiments may be provided to form additional third embodiments in which the first predefined condition and the second predefined condition include a detected establishment of unchanging temperature indicated by said temperature sensor and determined by said controller. Variations of the third embodiments may be provided to form additional third embodiments in which the temperature sensor is a contact-type temperature sensor that has a surface temperature element that engages an outside of an attached blood circuit.

According to fourth embodiments, the disclosed subject matter includes a method of regulating a patient body temperature. The method includes, at a first time: controlling, using an automatic controller, a rate of flow of blood through a flow channel connecting a patient to a temperature sensor to establish a first flow rate; at the first flow rate, permitting the flow of an unknown quantity of heat to or from the flow channel connecting a patient to a temperature sensor; at the first flow rate, measuring at least one temperature of the flow channel using the temperature sensor; recording a first temperature data responsively to said measuring; controlling, using the automatic controller, a rate of flow of blood through the first flow channel to establish a second flow rate, different from the first; repeating the permitting and measuring at the second flow rate and recording a second temperature data responsively to the corresponding measuring; calculating an extrapolated temperature from the first and second temperature data, the extrapolated temperature representing a temperature remote from the temperature sensor; and comparing the extrapolated temperature to data responsive to at least one reference temperature and outputting data to a user interface indicating data responsive to a result of said comparing. The method includes, at a second time, regulating a patient core temperature by adding or removing heat from the patient and/or patient's blood responsively to a result of the calculating.

Variations of the fourth embodiments may be provided to form additional fourth embodiments in which the establishing includes holding the respective first and second flow rates for a period of time effective to establish an unchanging temperature indicated by said temperature sensor. Variations of the fourth embodiments may be provided to form additional fourth embodiments in which the flow channel is an arterial line. Variations of the fourth embodiments may be provided to form additional fourth embodiments in which said controlling to establish a first flow rate and said controlling to establish a second flow rate include flowing at a respective rate for an interval effective to establish a steady state condition in terms of heat flow into or out of the fluid channel. Variations of the fourth embodiments may be provided to form additional fourth embodiments in which the flow channel is an arterial line. Variations of the fourth embodiments may be provided to form additional fourth embodiments in which the permitting includes permitting the flow of heat from the flow channel to the ambient environment through a blood carrying tube.

According to fifth embodiments, the disclosed subject matter includes a method of detecting a fever in a patient undergoing extracorporeal blood processing. The method includes, at a first time: controlling, using an automatic controller, a rate of flow of blood through a flow channel connecting a patient to a temperature sensor to establish a first flow rate; at the first flow rate, permitting the flow of an unknown quantity of heat to or from the flow channel connecting a patient to a temperature sensor; at the first flow rate, minimizing a flow of heat from or to the flow channel at the temperature sensor and while measuring at least one temperature of the flow channel using the temperature sensor, the minimizing including actively regulating a heat flux to minimize a heat flux from the flow channel through the temperature sensor; recording a first temperature data responsively to said measuring; controlling, using the automatic controller, a rate of flow of blood through the first flow channel to establish a second flow rate, different from the first; repeating the permitting, minimizing, and measuring at the second flow rate and recording a second temperature data responsively to the corresponding measuring; calculating an extrapolated temperature from the first and second temperature data, the extrapolated temperature representing a temperature remote from the temperature sensor; and comparing the extrapolated temperature to data responsive to at least one reference temperature and outputting data to a user interface indicating data responsive to a result of said comparing. The method includes, at a second time: regulating a patient core temperature by adding or removing heat from the patient and/or patient's blood responsively to a result of the calculating.

Variations of the fifth embodiments may be provided to form additional fifth embodiments in which the establishing includes holding the respective first and second flow rates for a period of time effective to establish an unchanging temperature indicated by said temperature sensor. Variations of the fifth embodiments may be provided to form additional fifth embodiments in which the flow channel is an arterial line. Variations of the fifth embodiments may be provided to form additional fifth embodiments in which said controlling to establish a first flow rate and said controlling to establish a second flow rate include flowing at a respective rate for an interval effective to establish a steady state condition in terms of heat flow into or out of the fluid channel. Variations of the fifth embodiments may be provided to form additional fifth embodiments in which the flow channel is an arterial line. Variations of the fifth embodiments may be provided to form additional fifth embodiments in which the permitting includes permitting the flow of heat from the flow channel to the ambient environment through a blood carrying tube.

According to sixth embodiments, the disclosed subject matter includes a method of determining a core in a patient undergoing extracorporeal blood processing. The method includes controlling, using an automatic controller, a rate of flow of blood through a flow channel connecting a patient to a temperature sensor to establish a first flow rate. The method includes at the first flow rate, permitting the flow of an unknown quantity of heat to or from the flow channel connecting a patient to a temperature sensor. The method includes, at the first flow rate, measuring at least one temperature of the flow channel using the temperature sensor. The method includes recording a first temperature data responsively to said measuring. The method includes controlling, using the automatic controller, a rate of flow of blood through the first flow channel to establish a second flow rate, different from the first. The method includes repeating the permitting and measuring at the second flow rate and recording a second temperature data responsively to the corresponding measuring. The method includes repeating the permitting and measuring at the third or further flow rates and recording a corresponding temperature data responsively to each of the corresponding measuring operations. The method includes calculating a temperature from the first, second, and third or further temperature data, the extrapolated temperature representing a temperature remote from the temperature sensor, the calculating including computationally fitting a predefine temperature decay function. The method includes comparing the calculated temperature to data responsive to at least one reference temperature and outputting data to a user interface indicating data responsive to a result of said comparing.

Variations of the sixth embodiments may be provided to form additional sixth embodiments in which the establishing includes holding the respective first and second flow rates for a period of time effective to establish an unchanging temperature indicated by said temperature sensor. Variations of the sixth embodiments may be provided to form additional sixth embodiments in which the flow channel is an arterial line. Variations of the sixth embodiments may be provided to form additional sixth embodiments in which said controlling to establish a first flow rate and said controlling to establish a second flow rate include flowing at a respective rate for an interval effective to establish a steady state condition in terms of heat flow into or out of the fluid channel. Variations of the sixth embodiments may be provided to form additional sixth embodiments in which the flow channel is an arterial line. Variations of the sixth embodiments may be provided to form additional sixth embodiments in which the permitting includes permitting the flow of heat from the flow channel to the ambient environment through a blood carrying tube.

According to seventh embodiments, the disclosed subject matter includes a blood treatment system that includes a blood treatment machine. The blood treatment machine has a programmable controller and at least a blood pump whose pumping rate is controlled by the controller. The blood treatment machine is arranged to receive a disposable blood circuit. The blood treatment machine has a plurality of temperature sensors positioned on the blood treatment machine and/or an attached blood circuit to measure respective temperatures of blood flowing through an attached blood circuit. The controller is programmed to establish a flow of blood at a first rate according to a first predefined condition, whereupon the controller records first temperature data representing a temperature indicated by said plurality of temperature sensors. The controller is programmed subsequently to establish a flow of blood at a second rate according to a second predefined condition, whereupon the controller records second temperature data representing a temperature indicated by said plurality of temperature sensors. The controller is further programmed to calculate a core patient temperature responsively to both said first and second temperature data, the core temperature calculation including fitting a decay function the temperatures indicated by said plurality of temperature sensors. The controller is further programmed to output a patient temperature signal to a user interface responsively to said patient temperature data.

Variations of the seventh embodiments may be provided to form additional seventh embodiments in which the patient temperature signal includes an indication that the patient has a fever. Variations of the seventh embodiments may be provided to form additional seventh embodiments in which the controller compares the patient temperature data to a predefined range and said patient temperature signal is responsive to a result of such a comparison. Variations of the seventh embodiments may be provided to form additional seventh embodiments in which the first predefined condition and the second predefined condition are time intervals. Variations of the seventh embodiments may be provided to form additional seventh embodiments in which the first predefined condition and the second predefined condition are identical time intervals. Variations of the seventh embodiments may be provided to form additional seventh embodiments in which the first predefined condition and the second predefined condition include a detected establishment of unchanging temperature indicated by said temperature sensor and determined by said controller. Variations of the seventh embodiments may be provided to form additional seventh embodiments in which the temperature sensor is a contact-type temperature sensor that has a surface temperature element that engages an outside of an attached blood circuit.

According to eight embodiments, the disclosed subject matter includes a blood with a blood pump and a temperature sensor. The blood pump and temperature sensor are configured to receive a predefined fluid circuit having a blood circuit. The blood circuit may or may not form part of the disclosed embodiment but the form of the embodiment may be limited by the predefined blood circuit. A controller connects to the blood pump to control a speed thereof and to the temperature sensor to receive a temperature signal output therefrom. The temperature sensor is configured to detect a temperature of blood carried by the blood circuit. the controller is programmed to operate the pump at at least two flow rates, record first and second temperature data responsive to the temperature signal at each flow rate, respectively and to calculate a core temperature, responsive to both the first and second temperature data, where the core temperature is an estimation of the temperature at a point in said blood circuit remote from the temperature sensor and compensates for a temperature change in flowing blood between said point and said temperature sensor.

Variations of the eighth embodiments may be provided to form additional eighth embodiments in which the controller is connected to a user interface with a display and is further programmed to show said core temperature on said display. Variations of the eighth embodiments may be provided to form additional eighth embodiments that include a treatment fluid pump connected for control by said controller, the treatment fluid pump engaging a treatment fluid circuit of said predefined fluid circuit. The controller may be further programmed to operate said blood pump at said at least two flow rates during a temperature measurement phase of a startup mode of said blood treatment system. Variations of the eighth embodiments may be provided to form additional eighth embodiments in which in the temperature measurement phase of the startup mode the controller controls the treatment fluid pump to prevent flow in the treatment fluid circuit. Variations of the eighth embodiments may be provided to form additional eighth embodiments in which the predefined fluid circuit has treatment device that forms a heat transfer interface between the treatment fluid circuit and the blood circuit such that heat is transferred between the blood in the blood circuit and treatment fluid in the treatment fluid circuit. Variations of the eighth embodiments may be provided to form additional eighth embodiments that include a temperature regulator that engages the treatment fluid circuit. The controller controls the temperature regulator to bring a treatment fluid to a predefined temperature in said treatment fluid device prior to said temperature measurement phase. Variations of the eighth embodiments may be provided to form additional eighth embodiments in which the controller is configured to control the temperature regulator and flushes the treatment device prior to said treatment measurement phase to fill a blood compartment of said treatment device with treatment fluid at said predefined temperature. Variations of the eighth embodiments may be provided to form additional eighth embodiments in which the predefined temperature is a normal body temperature. Variations of the eighth embodiments may be provided to form additional eighth embodiments in which the controller is programmed to calculate a core temperature based on a constant heat transfer rate for all of said at least two flow rates. Variations of the eighth embodiments may be provided to form additional eighth embodiments in which the controller is programmed to calculate a core temperature responsively to an initial estimate of the core temperature that is based on the constant heat transfer rate and responsively to an improved core temperature estimate responsively to the initial estimate of the core temperature, an estimated or measured of an ambient temperature, and the at least two flow rates. Variations of the eighth embodiments may be provided to form additional eighth embodiments in which the improved core temperature estimate is responsive to a difference between the estimated or measured ambient temperature and an average of the initial estimate of the core temperature and the temperature indicated by said temperature signal.

According to ninth embodiments, the disclosed subject matter includes a blood treatment method. The method includes providing a blood pump and a temperature sensor, the blood pump and temperature sensor is configured to receive a predefined fluid circuit having a blood circuit. The method includes providing a controller connected to the blood pump to control a speed thereof and to the temperature sensor to receive a temperature signal output therefrom. The temperature sensor is configured to detect a temperature of blood carried by the blood circuit. The method includes using the controller, operating the pump at at least two flow rates. The method includes, for each of the at least two flow rates, using the controller, recording first and second temperature data responsive to the temperature signal at each of said at least two flow rates. The method includes using the controller, calculating a core temperature responsively to both the first and second temperature data such that the core temperature is an estimation of the temperature at a point in said blood circuit remote from the temperature sensor and the calculating compensates for a temperature change in flowing blood between said point and said temperature sensor.

Variations of the ninth embodiments may be provided to form additional ninth embodiments that include using the controller display said core temperature a display of a user interface. Variations of the ninth embodiments may be provided to form additional ninth embodiments that include using the controller, controlling a treatment fluid pump connected, the treatment fluid pump engaging a treatment fluid circuit of said predefined fluid circuit and controlling a treatment fluid pump includes operating said blood pump at said at least two flow rates during a temperature measurement phase of a startup mode of said blood treatment system, the startup mode includes priming said blood circuit. Variations of the ninth embodiments may be provided to form additional ninth embodiments in which, during temperature measurement phase of the startup mode, using the controller, controlling the treatment fluid pump to prevent flow in the treatment fluid circuit. Variations of the ninth embodiments may be provided to form additional ninth embodiments in which the predefined fluid circuit has treatment device that forms a heat transfer interface between the treatment fluid circuit and the blood circuit such that heat is transferred between the blood in the blood circuit and treatment fluid in the treatment fluid circuit. Variations of the ninth embodiments may be provided to form additional ninth embodiments in which a temperature regulator engages the treatment fluid circuit, further comprising, using the controller, controlling the temperature regulator and said treatment fluid pump, bringing a treatment fluid to a predefined temperature in said treatment fluid device prior to said temperature measurement phase. Variations of the ninth embodiments may be provided to form additional ninth embodiments that include, using the controller, controlling the temperature regulator and flushes the treatment device prior to said treatment measurement phase to fill a blood compartment of said treatment device with treatment fluid at said predefined temperature. Variations of the ninth embodiments may be provided to form additional ninth embodiments in which the predefined temperature is a normal body temperature. Variations of the ninth embodiments may be provided to form additional ninth embodiments in which the calculating a core temperature includes calculating based on a constant heat transfer rate for all of said at least two flow rates. Variations of the ninth embodiments may be provided to form additional ninth embodiments in which the calculating includes calculating a core temperature responsively to an initial estimate of the core temperature that is based on the constant heat transfer rate and responsively to an improved core temperature estimate responsively to the initial estimate of the core temperature, an estimated or measured of an ambient temperature, and the at least two flow rates. Variations of the ninth embodiments may be provided to form additional ninth embodiments in which the improved core temperature estimate is responsive to a difference between the estimated or measured ambient temperature and an average of the initial estimate of the core temperature and the temperature indicated by said temperature signal.

According to tenth embodiments, the disclosed subject matter includes a method of detecting a blood temperature in a blood treatment circuit. The method includes estimating a steady state heat transfer characteristic of a fluid circuit, the estimate is calculated inferentially from a temperature measurement of a fluid flow in a blood circuit. The method includes storing said heat transfer characteristic and calculating from it, a temperature at a point in said blood circuit remote from a point where the temperature measurement was taken. The method includes measuring a change in the temperature and calculating whether that change indicates a possible change in the heat transfer characteristic. The method includes repeating said estimating responsively to an outcome of said calculating.

According to eleventh embodiments, the disclosed subject matter includes, a blood treatment system. A blood pump and a temperature sensor, the blood pump and temperature sensor is configured to receive a predefined fluid circuit has a blood circuit with a blood inlet. A controller is connected to the blood pump to control a speed thereof and to the temperature sensor to receive a temperature signal output therefrom. The temperature sensor is configured to detect a temperature of blood carried by the blood circuit. The controller is programmed to operate the pump at at least two flow rates, record first and second temperature data responsive to the temperature signal at each flow rate, respectively and to calculate an inlet temperature at the blood inlet, responsive to both the first and second temperature data, where the inlet temperature is an estimation of the temperature at a point in the blood circuit remote from the temperature sensor and compensates for a temperature change in flowing blood between the point and the temperature sensor. Further eleventh embodiments include ones in which the controller is connected to a user interface with a display and is further programmed to show the inlet temperature on the display.

Further eleventh embodiments include ones that include a treatment fluid pump connected for control by the controller, the treatment fluid pump engaging a treatment fluid circuit of the predefined fluid circuit. The controller is further programmed to operate the blood pump at the at least two flow rates during a temperature measurement phase of a startup mode of the blood treatment system.

Further eleventh embodiments include ones in which in the temperature measurement phase of the startup mode the controller controls the treatment fluid pump to prevent flow in the treatment fluid circuit.

Further eleventh embodiments include ones in which the predefined fluid circuit has a treatment device that forms a heat transfer interface between the treatment fluid circuit and the blood circuit such that heat is transferred between the blood in the blood circuit and treatment fluid in the treatment fluid circuit.

Further eleventh embodiments include ones that include a temperature regulator that engages the treatment fluid circuit, wherein the controller controls the temperature regulator to bring a treatment fluid to a predefined temperature in the treatment fluid device prior to the temperature measurement phase.

Further eleventh embodiments include ones in which the controller is configured to control the temperature regulator and flushes the treatment device prior to the treatment measurement phase to fill a blood compartment of the treatment device with treatment fluid at the predefined temperature.

Further eleventh embodiments include ones in which the predefined temperature is a normal body temperature.

Further eleventh embodiments include ones in which the controller is programmed to calculate the inlet temperature based on a constant heat transfer rate for all of the at least two flow rates.

Further eleventh embodiments include ones in which the controller is programmed to calculate the inlet temperature responsively to an initial estimate of the inlet temperature that is based on the constant heat transfer rate and responsively to an improvement in the inlet temperature estimate responsively to the initial estimate of the inlet temperature, an estimated or measured of an ambient temperature, and the at least two flow rates.

Further eleventh embodiments include ones in which the improved inlet temperature estimate is responsive to a difference between the estimated or measured ambient temperature and an average of the initial estimate of the inlet temperature and the temperature indicated by the temperature signal.

According to twelfth embodiments, the disclosed subject matter includes, a blood treatment method. The method includes providing a blood pump and a temperature sensor, the blood pump and temperature sensor is configured to receive a predefined fluid circuit has a blood circuit with a blood inlet. The method further includes providing a controller connected to the blood pump to control a speed thereof and to the temperature sensor to receive a temperature signal output therefrom. The temperature sensor is configured to detect a temperature of blood carried by the blood circuit. The method further includes using the controller, operating the pump at at least two flow rates. The method further includes, for each of the at least two flow rates, using the controller, recording first and second temperature data responsive to the temperature signal at each of the at least two flow rates. The method further includes using the controller, calculating an inlet temperature responsively to both the first and second temperature data such that the inlet temperature is an estimation of the temperature at a point in the blood circuit remote from the temperature sensor and the calculating compensates for a temperature change in flowing blood between the point and the temperature sensor.

Further twelfth embodiments include ones in which using the controller display the inlet temperature a display of a user interface.

Further twelfth embodiments include ones that include using the controller, controlling a treatment fluid pump connected, the treatment fluid pump engaging a treatment fluid circuit of the predefined fluid circuit. controlling a treatment fluid pump includes operating the blood pump at the at least two flow rates during a temperature measurement phase of a startup mode of the blood treatment system, the startup mode includes priming the blood circuit.

Further twelfth embodiments include ones in which during temperature measurement phase of the startup mode, using the controller, controlling the treatment fluid pump to prevent flow in the treatment fluid circuit.

Further twelfth embodiments include ones in which the predefined fluid circuit has treatment device that forms a heat transfer interface between the treatment fluid circuit and the blood circuit such that heat is transferred between the blood in the blood circuit and treatment fluid in the treatment fluid circuit.

Further twelfth embodiments include ones in which a temperature regulator engages the treatment fluid circuit, further comprising, using the controller, controlling the temperature regulator and the treatment fluid pump, bringing a treatment fluid to a predefined temperature in the treatment fluid device prior to the temperature measurement phase.

Further twelfth embodiments include ones that include using the controller, controlling the temperature regulator and flushes the treatment device prior to the treatment measurement phase to fill a blood compartment of the treatment device with treatment fluid at the predefined temperature.

Further twelfth embodiments include ones in which the predefined temperature is a normal body temperature.

Further twelfth embodiments include ones in which the calculating the inlet temperature includes calculating based on a constant heat transfer rate for all of the at least two flow rates.

Further twelfth embodiments include ones in which the calculating the inlet temperature is responsive to an initial estimate of the inlet temperature that is based on the constant heat transfer rate and responsively to an improved inlet temperature estimate responsively to the initial estimate of the inlet temperature, an estimated or measured of an ambient temperature, and the at least two flow rates.

Further twelfth embodiments include ones in which the improved inlet temperature estimate is responsive to a difference between the estimated or measured ambient temperature and an average of the initial estimate of the inlet temperature and the temperature indicated by the temperature signal.

According to thirteenth embodiments, the disclosed subject matter includes, a method of detecting a blood temperature in a blood treatment circuit. The method includes estimating a steady state heat transfer characteristic of a fluid circuit, the estimate is calculated inferentially from a temperature measurement of a fluid flow in a blood circuit. The method further includes storing the heat transfer characteristic and calculating from it, a temperature at a point in the blood circuit remote from a point where the temperature measurement was taken. The method further includes measuring a change in the temperature and calculating whether that change indicates a possible change in the heat transfer characteristic. The method further includes repeating the estimating responsively to an outcome of the calculating.

According to fourteenth embodiments, the disclosed subject matter includes a fluid temperature method. The method includes providing a fluid pump and a temperature sensor, the fluid pump and temperature sensor is configured to receive a predefined fluid circuit. The method further includes providing a controller connected to the fluid pump to control a speed thereof and to the temperature sensor to receive a temperature signal output therefrom. The method further includes the temperature sensor is configured to detect a temperature of fluid carried by the fluid circuit. The method further includes using the controller, operating the pump at at least two flow rates. The method further includes, for each of the at least two flow rates, using the controller, recording first and second temperature data responsive to the temperature signal at each of the at least two flow rates. The method further includes using the controller, calculating an inlet temperature responsively to both the first and second temperature data such that the inlet temperature is an estimation of the temperature at a point in the fluid circuit remote from the temperature sensor and the calculating compensates for a temperature change in flowing fluid between the point and the temperature sensor. Further fourteenth embodiments include ones that include using the controller, displaying the inlet temperature a display of a user interface.

Further fourteenth embodiments include ones that include using the controller, controlling a treatment fluid pump connected, the treatment fluid pump engaging a treatment fluid circuit of the predefined fluid circuit. controlling a treatment fluid pump includes operating the fluid pump at the at least two flow rates during a temperature measurement phase of a startup mode of the fluid treatment system, the startup mode includes priming the fluid circuit.

Further fourteenth embodiments include ones in which, during temperature measurement phase of the startup mode, using the controller, controlling the treatment fluid pump to prevent flow in the treatment fluid circuit.

Further fourteenth embodiments include ones in which the predefined fluid circuit has treatment device that forms a heat transfer interface between the treatment fluid circuit and the fluid circuit such that heat is transferred between the fluid in the fluid circuit and treatment fluid in the treatment fluid circuit.

Further fourteenth embodiments include ones in which a temperature regulator engages the treatment fluid circuit, further comprising, using the controller, controlling the temperature regulator and the treatment fluid pump, bringing a treatment fluid to a predefined temperature in the treatment fluid device prior to the temperature measurement phase.

Further fourteenth embodiments include ones that include, using the controller, controlling the temperature regulator and flushes the treatment device prior to the treatment measurement phase to fill a fluid compartment of the treatment device with treatment fluid at the predefined temperature.

Further fourteenth embodiments include ones in which the predefined temperature is a normal body temperature.

Further fourteenth embodiments include ones in which the calculating an inlet temperature includes calculating based on a constant heat transfer rate for all of the at least two flow rates.

Further fourteenth embodiments include ones in which the calculating includes calculating the inlet temperature responsively to an initial estimate of the inlet temperature that is based on the constant heat transfer rate and responsively to an improved inlet temperature estimate responsively to the initial estimate of the inlet temperature, an estimated or measured of an ambient temperature, and the at least two flow rates.

Further fourteenth embodiments include ones in which the improved inlet temperature estimate is responsive to a difference between the estimated or measured ambient temperature and an average of the initial estimate of the inlet temperature and the temperature indicated by the temperature signal.

Further fourteenth embodiments include ones in which the fluid is blood.

Further fourteenth embodiments include ones in which the fluid is spent peritoneal dialysate.

Further fourteenth embodiments include ones in which the fluid is urine.

Further fourteenth embodiments include ones in which the treatment fluid is dialysate.

Further fourteenth embodiments include ones in which the treatment fluid is a gas.

According to fifteenth embodiments, the disclosed subject matter includes, a method of estimating a temperature $T_p$ of the blood of a patient connected to an extracorporeal blood treatment device, the method is implemented automatically by a controller operable with the extracorporeal blood treatment device, the controller is connected to a pump, a sensor, and a user interface. The method includes using the controller, pumping blood in a blood circuit from a patient access through the blood circuit to a temperature sensor positioned along the blood circuit remote from the patient access such that heat is transferred between the blood and the external environment of the blood circuit as the blood flows from the access to the temperature sensor. The pumping includes, automatically, using the controller, pumping blood at a first flow rate $F_1$ and then subsequently pumping blood at a second flow rate $F_2$, recording temperatures $T_{c1}$ and $T_{c2}$, respectively, for each of the flow rates, calculating a temperature $T_p$ from temperatures $T_{c1}$ and $T_{c2}$ and flows $F_1$ and $F_2$, and outputting data responsive to the calculated $T_p$.

Further fifteenth embodiments include ones in which the calculating is independent of a measured temperature of the external environment.

Further fifteenth embodiments include ones in which the calculating initially uses an estimated or standard temperature of the external environment but calculates an effective temperature of the external environment.

Further fifteenth embodiments include ones in which the calculating includes calculating $T_p$ by finding a common intercept of two lines, each is proportional to the same constant heat transfer rate and inversely proportional, respectively, to $F_1$ and $F_2$.

Further fifteenth embodiments include ones in which $T_p$ is calculating from: $T_p=[(T_{c1}*F_1)-(T_{c2}*F_2)]/(F_1-F_2)$.

Further fifteenth embodiments include ones in which $F_1$ is a maximum safe blood flow rate of the extracorporeal blood treatment device.

Further fifteenth embodiments include ones in which $F_2$ is between 40 and 60% of $F_1$.

Further fifteenth embodiments include ones in which $F_2$ is between 50% of $F_1$.

Further fifteenth embodiments include ones that include revising the estimate of $T_p$ before the outputting, the revising includes using an initial estimate of the temperature of the environment, iteratively solving for an effective temperature of the environment.

Further fifteenth embodiments include ones that include revising the estimate of $T_p$ before the outputting, the revising includes using an initial estimate of the temperature of the environment to calculate independent heat transfer rates corresponding to each of the conditions corresponding to $T_{c1}$ and $T_{c2}$.

Further fifteenth embodiments include ones in which the revising further includes iteratively refining the estimate of Tb using a single temperature of the environment.

Further fifteenth embodiments include ones in which the revising further includes iteratively refining the estimate of Tb by estimating $T_a$=temperature of the environment and solving for a power rate equal to a ratio of a characteristic temperature of the blood at each of $F_1$ and $F_2$, the characteristic temperature depending on a prior estimate of $T_p$, and using the power rate to calculate an updated estimate of $T_p$ and then repeating with the updated estimate until it converges.

Further fifteenth embodiments include ones in which the using the power rate includes calculating $T_p*=[(T_{c1}*F_1)-(Pr\ T_{c2}*F_2)]/[F_1-(Pr*F_2)]$, where Pr is the most recent power rate and $T_p*$ is a new estimate for $T_p$.

Further fifteenth embodiments include ones in which Pr is calculated at each iteration according to $Pr=(T_{b1}-T_a)/(T_{b2}-T_a)$, where $T_{b1}=(T_p+T_{c1})/2$, $T_{b2}=(T_p+T_{c2})/2$, and $T_a$ is the temperature of the environment.

Further fifteenth embodiments include ones in which Pr is calculated at each iteration according to $Pr=LMTD(T_{c1}, T_p^*, T_a)/LMTD(T_{c2}, T_p^*, T_a)$, where $LMTD(Tc, T_p, T_a)=(T_c-T_a)-(T_p-T_a)/\ln[(Tc-T_a)/(T_p-T_a)]$.

According to sixteenth embodiments, the disclosed subject matter includes, a method of estimating a temperature $T_p$ of the blood of a patient connected to an extracorporeal blood treatment device, the method is implemented automatically by a controller operable with the extracorporeal blood treatment device, the controller is connected to a pump, a sensor, and a user interface. The method includes using the controller, pumping blood from a patient access through a blood circuit to a temperature sensor positioned along the blood circuit remote from the patient access such that heat is transferred between the blood and the external environment of the blood circuit as the blood flows from the access to the temperature sensor. The pumping includes, automatically, using the controller, pumping blood at a first flow rate $F_1$ and then subsequently pumping blood at a second flow rate $F_2$, recording temperatures $T_{c1}$ and $T_{c2}$, respectively, for each of the flow rates, calculating a temperature $T_p$ from temperatures $T_{c1}$ and $T_{c2}$ and flows $F_1$ and $F_2$, wherein the calculating implicitly employs an effective temperature difference between the blood temperature and an effective temperature of the external environment of the blood circuit for each of the $F_1$ and $F_2$.

Further sixteenth embodiments include ones in which the effective temperature of the environment is a temperature that is calculated based on the assumption of a uniform temperature of the external environment of the blood circuit that agrees with the measured temperatures.

Further sixteenth embodiments include ones in which the effective temperature of the environment is a temperature that is calculated based on the assumption of a uniform temperature of the external environment of the blood circuit that agrees with the measured temperatures the effective temperature of the environment is iteratively calculated.

Further sixteenth embodiments include ones in which the methods are carried out automatically by a computer connected to a blood processing machine.

Further sixteenth embodiments include ones in which the methods are carried out automatically by a computer connected to a hemodialysis machine.

Further sixteenth embodiments include ones in which the methods are carried out automatically by a computer connected to a dialysis machine.

According to seventeenth embodiments, the disclosed subject matter includes, a method of calculating a blood return temperature. The method includes pumping blood from a patient using an extracorporeal blood processing machine, the pumping includes pumping blood at multiple flow rates. The method further includes measuring blood temperatures in a blood circuit at a first temperature sensor located remote from a patient access, connected by an arterial portion thereof, for each of the multiple flow rates. The method further includes calculating a heat transfer characteristic of the blood circuit from the patient access to the first temperature sensor responsively to the multiple flow rates and the respective temperatures. The method further includes calculating a return temperature at a patient access end of a venous portion of the blood circuit that returns blood to the patient.

Further seventeenth embodiments include ones in which the calculating a return temperature includes measuring a temperature at a second temperature located remote from the patient access and connected by the venous portion of the blood circuit.

Further seventeenth embodiments include ones in which the venous and arterial portions of the blood circuit are parallel channels.

Further seventeenth embodiments include ones in which the venous and arterial portions of the blood circuit are parallel tubes over a major fraction thereof.

Further seventeenth embodiments include ones in which temperature sensor is an active temperature sensor that measures temperature by actively canceling heat flux in a wall of a fluid circuit separating a temperature sensor and the fluid whose temperature is to be measured.

Further seventeenth embodiments include ones that include using a controller of the extracorporeal blood processing machine, calculating a heat transfer parameter of the blood circuit, the heat transfer parameter is responsive to a thermal resistance of a wall of the blood circuit.

According to eighteenth embodiments, the disclosed subject matter includes, a method of calculating a blood return temperature. The method includes pumping blood from a patient using an extracorporeal blood processing machine, the pumping includes pumping blood at multiple flow rates. The method further includes measuring blood temperatures, and recording them, in a blood circuit at a first temperature sensor located remote from a patient access, connected by an arterial portion thereof, for each of the multiple flow rates. The method further includes calculating a heat transfer characteristic of the blood circuit from the patient access to the first temperature sensor responsively to the multiple flow rates and the respective temperatures. The method further includes using the heat transfer characteristic, regulating a return temperature at a patient access end of a venous portion of the blood circuit that returns blood to the patient.

Further eighteenth embodiments include ones in which the regulating is effective to maintain a body temperature of a patient in a predefined range.

Further eighteenth embodiments include ones in which the regulating includes compensating for heat transfer in the venous portion between blood carried thereby and an external environment of the venous portion.

Further eighteenth embodiments include ones that include detecting a condition indicating that the heat transfer characteristic has changed and, responsively thereto, repeating the pumping blood at multiple flow rates and calculating a heat transfer characteristic responsively to a result of the detecting.

Further eighteenth embodiments include ones in which the detecting a condition includes a predefined change in the temperature indicated by the first temperature sensor.

Further eighteenth embodiments include ones in which the detecting includes detecting a mechanical movement of the blood circuit.

Further eighteenth embodiments include ones that include detecting a steady state of the heat transfer characteristic, wherein the recording is responsive to the detecting a stead state.

According to nineteenth embodiments, the disclosed subject matter includes, a method of calculating a patient blood temperature. The method includes pumping blood from a patient using an extracorporeal blood processing machine, the pumping includes pumping blood at multiple flow rates. The method further includes measuring blood temperatures in a blood circuit at a first temperature sensor located remote from a patient access, connected by an arterial portion thereof, for each of the multiple flow rates. The method further includes calculating a heat transfer characteristic of the blood circuit from the patient access to the first temperature sensor responsively to the multiple flow rates and the respective temperatures. The method further includes using the heat transfer characteristic, calculating a patient body temperature includes compensating for heat transfer between the patient access and the temperature sensor based on the heat transfer characteristic.

Further nineteenth embodiments include ones in which the heat transfer characteristic is responsive to a heat transfer coefficient and a temperature of an environment of the arterial portion.

Further nineteenth embodiments include ones that include recording the calculating body temperature to a treatment log corresponding to the patient.

Further nineteenth embodiments include ones that include outputting a signal responsively to a comparison between data in the treatment log and a temperature resulting from the calculating.

Further nineteenth embodiments include ones that include recording the calculating body temperature to a treatment log corresponding to the patient, the recording includes recording a time series of temperatures over an interval of a treatment.

Further nineteenth embodiments include ones that include outputting a signal responsively to a comparison between data in the treatment log and a temperature resulting from the calculating.

Further nineteenth embodiments include ones that include repeating the pumping blood at multiple flow rates and calculating a heat transfer characteristic of the blood circuit in response to the lapse of a timer.

Further nineteenth embodiments include ones that include repeating the pumping blood at multiple flow rates and calculating a heat transfer characteristic of the blood circuit in response to the lapse of a timer initialized at the beginning of a blood treatment.

In any of the disclosed embodiments, any recited calculations may be performed by the controller of a blood processing machine.

According to twentieth embodiments, the disclosed subject matter includes, a blood treatment system. The system includes a controller, a blood pump and a temperature sensor, the blood pump and temperature sensor is configured to receive a predefined fluid circuit has a blood circuit with a blood inlet. The controller is connected to the blood pump to control a speed thereof and to the temperature sensor to receive a temperature signal output therefrom. The temperature sensor is configured to detect a temperature of blood carried by the blood circuit. The controller is programmed operate the pump at at least two flow rates during a temperature measurement operation. For each of the at least two flow rates, the controller records first and second temperature data responsive to the temperature signal at each of the at least two flow rates. The controller calculates an inlet temperature responsively to both the first and second temperature data such that the inlet temperature is an estimation of the temperature at a point in the blood circuit remote from the temperature sensor where the calculation compensates for a temperature change in flowing blood between the point and the temperature sensor.

Further twentieth embodiments include ones in which the controller displays the inlet temperature a display of a user interface.

Further twentieth embodiments include ones in which the controller controls a treatment fluid pump connected, the treatment fluid pump engaging a treatment fluid circuit of the predefined fluid circuit and controls a treatment fluid pump and operates the blood pump at the at least two flow rates during a temperature measurement phase of a startup mode of the blood treatment system, the startup mode includes priming the blood circuit.

Further twentieth embodiments include ones in which, during the temperature measurement phase of the startup mode, the controller controls the treatment fluid pump to prevent flow in the treatment fluid circuit.

Further twentieth embodiments include ones in which the predefined fluid circuit has treatment device that forms a heat transfer interface between the treatment fluid circuit and the blood circuit such that heat is transferred between the blood in the blood circuit and treatment fluid in the treatment fluid circuit.

Further twentieth embodiments include ones in which a temperature regulator engages the treatment fluid circuit and the controller controls the temperature regulator and the treatment fluid pump, bringing a treatment fluid to a predefined temperature in the treatment fluid device prior to the temperature measurement phase.

Further twentieth embodiments include ones in which the controller controls the temperature regulator and flushes the treatment device prior to the treatment measurement phase to fill a blood compartment of the treatment device with treatment fluid at the predefined temperature.

Further twentieth embodiments include ones in which the predefined temperature is a normal body temperature.

Further twentieth embodiments include ones in which the inlet temperature is calculated based on a constant heat transfer rate for all of the at least two flow rates.

Further twentieth embodiments include ones in which the inlet temperature is calculated responsive to an initial estimate of the inlet temperature that is based on the constant heat transfer rate and responsively to an improved inlet temperature estimate responsively to the initial estimate of the inlet temperature, an estimated or measured of an ambient temperature, and the at least two flow rates.

Further twentieth embodiments include ones in which the improved inlet temperature estimate is responsive to a difference between the estimated or measured ambient temperature and an average of the initial estimate of the inlet temperature and the temperature indicated by the temperature signal.

According to twenty-first embodiments, the disclosed subject matter includes, a system for detecting a blood temperature in a blood treatment circuit. A blood treatment machine has a controller, the controlling is programmed to estimate a steady state heat transfer characteristic of a fluid circuit attached to the blood treatment machine to generate an estimate by calculating inferentially from a temperature measurements of a blood flow in a blood circuit and corresponding blood flow rates. The controller stores the heat transfer characteristic and calculating from it, a temperature at a point in the blood circuit remote from a point where the temperature measurement was taken. The controller further measures a change in the temperature and calculating whether that change indicates a possible change in the heat transfer characteristic and repeating the estimating responsively to an outcome of the calculating.

According to twenty-second embodiments, the disclosed subject matter includes, a fluid temperature system. A fluid system has a fluid pump and a temperature sensor. The fluid pump and temperature sensor are configured to receive a predefined fluid circuit. A controller is connected to the fluid pump to control a speed thereof and to the temperature sensor to receive a temperature signal output therefrom. The temperature sensor is configured to detect a temperature of fluid carried by the fluid circuit. The controller operates the pump at at least two flow rates. For each of the at least two flow rates, the controller records first and second temperature data responsive to the temperature signal at each of the at least two flow rates. The controller calculates an inlet temperature responsively to both the first and second temperature data such that the inlet temperature is an estimation of the temperature at a point in the fluid circuit remote from the temperature sensor. The calculating compensates for a temperature change in flowing fluid between the point and the temperature sensor.

Further twenty-second embodiments include ones in which the controller displays the inlet temperature a display of a user interface.

Further twenty-second embodiments include ones in which the calculating includes calculating the inlet temperature responsively to an initial estimate of the inlet temperature that is based on the constant heat transfer rate and responsively to an improved inlet temperature estimate responsively to the initial estimate of the inlet temperature, an estimated or measured of an ambient temperature, and the at least two flow rates.

Further twenty-second embodiments include ones in which the improved inlet temperature estimate is responsive to a difference between the estimated or measured ambient temperature and an average of the initial estimate of the inlet temperature and the temperature indicated by the temperature signal.

According to twenty-third embodiments, the disclosed subject matter includes, a system for performing a blood treatment. An extracorporeal blood treatment device has a controller controlling the extracorporeal blood treatment device, the controller is connected to a pump, a sensor, and a user interface. The controller pumps blood from a patient access through a blood circuit to a temperature sensor positioned along the blood circuit remote from the patient access such that heat is transferred between the blood and the external environment of the blood circuit as the blood flows from the access to the temperature sensor. The controller pumps blood at a first flow rate $F_1$ and then subsequently pumping blood at a second flow rate $F_2$, records temperatures $T_{c1}$ and $T_{c2}$, respectively, for each of the flow rates, calculates a temperature $T_p$ from temperatures $T_{c1}$ and $T_{c2}$ and flows $F_1$ and $F_2$, and outputs data responsive to the calculated $T_p$.

Further twenty-third embodiments include ones in which the calculating is independent of a measured temperature of the external environment.

Further twenty-third embodiments include ones in which the calculating initially uses an estimated or standard temperature of the external environment but calculates an effective temperature of the external environment.

Further twenty-third embodiments include ones in which the calculating includes calculating $T_p$ by finding a common intercept of two lines, each is proportional to the same constant heat transfer rate and inversely proportional, respectively, to $F_1$ and $F_2$.

Further twenty-third embodiments include ones in which $T_p$ is calculating from: $T_p = [(T_{c1}*F_1) - (T_{c2}*F_2)]/(F_1 - F_2)$.

Further twenty-third embodiments include ones in which $F_1$ is a maximum safe blood flow rate of the extracorporeal blood treatment device.

Further twenty-third embodiments include ones in which $F_2$ is between 40 and 60% of $F_1$.

Further twenty-third embodiments include ones in which $F_2$ is between 50% of $F_1$.

Further twenty-third embodiments include ones in which the controller revises the estimate of $T_p$ before the outputting includes using an initial estimate of the temperature of the environment, iteratively solving for an effective temperature of the environment.

Further twenty-third embodiments include ones in which the estimate of $T_p$ is revised before outputting and includes using an initial estimate of the temperature of the environment to calculate independent heat transfer rates corresponding to each of the conditions corresponding to $T_{c1}$ and $T_{c2}$.

Further twenty-third embodiments include ones in which the estimate is revised by iteratively refining the estimate of $T_b$ using a single temperature of the environment.

Further twenty-third embodiments include ones in which the controller iteratively refines the estimate of $T_b$ by estimating $T_a$=temperature of the environment and solving for a power rate equal to a ratio of a characteristic temperature of the blood at each of $F_1$ and $F_2$, the characteristic temperature depending on a prior estimate of $T_p$, and using the power rate to calculate an updated estimate of $T_p$ and then repeating with the updated estimate until it converges.

Further twenty-third embodiments include ones in which the power rate is used, at least in part, by calculating $T_p^* = [(T_{c1}*F_1) - (Pr\ T_{c2}*F_2)]/[F_1 - (Pr*F_2)]$, where Pr is the most recent power rate and $T_p^*$ is a new estimate for $T_p$.

Further twenty-third embodiments include ones in which Pr is calculated at each iteration according to $Pr = (T_{b1} - T_a)/(T_{b2} - T_a)$, where $T_{b1} = (T_p + T_{c1})/2$, $T_{b2} = (T_p + T_{c2})/2$, and $T_a$ is the temperature of the environment.

Further twenty-third embodiments include ones in which Pr is calculated at each iteration according to $Pr = LMTD(T_{c1}, T_p^*, T_a)/LMTD(T_{c2}, T_p^*, T_a)$, where $LMTD(T_c, T_p, T_a) = (T_c - T_a) - (T_p - T_a)/\ln[(T_c - T_a)/(T_p - T_a)]$.

According to twenty-fourth embodiments, the disclosed subject matter includes, a system for performing a blood treatment. An extracorporeal blood treatment device estimates a temperature $T_p$ of the blood of a patient connected to the extracorporeal blood treatment device, the extracorporeal blood treatment device includes a controller the controller is connected to a pump, a sensor, and a user interface. The controller is programmed or otherwise configured to implement a method, automatically, that includes: pumping blood from a patient access through a blood circuit to a temperature sensor positioned along the blood circuit remote from the patient access such that heat is transferred between the blood and the external environment of the blood circuit as the blood flows from the access to the temperature sensor the pumping blood is effective to convey blood at a first flow rate $F_1$ and then subsequently convey blood at a second flow rate $F_2$. The method further includes recording temperatures $T_{c1}$ and $T_{c2}$, respectively, for each of the flow rates and calculating a temperature $T_p$ from temperatures $T_{c1}$ and $T_{c2}$ and flows $F_1$ and $F_2$. The calculating implicitly includes using an effective temperature difference between the blood temperature and an effective temperature of the external environment of the blood circuit for each of the $F_1$ and $F_2$.

Further twenty-fourth embodiments include ones in which the effective temperature of the environment is a temperature that is calculated based on the assumption of a uniform temperature of the external environment of the blood circuit that agrees with the measured temperatures.

Further twenty-fourth embodiments include ones in which the effective temperature of the environment is a temperature that is calculated based on the assumption of a uniform temperature of the external environment of the blood circuit that agrees with the measured temperatures the effective temperature of the environment is iteratively calculated.

According to twenty-fifth embodiments, the disclosed subject matter includes, a blood processing system capable of calculating a blood return temperature. A blood pump is adapted to receive a blood circuit and is connected to a controller that controls the blood pump to pump blood from a patient at multiple flow rates during a temperature measurement sequence. The controller is connected to receive and store temperature data indicating blood temperatures in an attached blood circuit from a first temperature sensor located remotely from a patient access end of the blood circuit, the patient access is connected by an arterial portion of the blood circuit, the temperature data is stored for each of the multiple flow rates. The controller calculates a heat transfer characteristic of the blood circuit from the patient access to the first temperature sensor responsively to the multiple flow rates and the respective temperatures. The controller calculates a return temperature at a patient access end of a venous portion of the blood circuit that returns blood to the patient.

Further twenty-fifth embodiments include ones in which the calculating a return temperature includes measuring a temperature at a second temperature located remote from the patient access and connected by the venous portion of the blood circuit.

Further twenty-fifth embodiments include ones in which the venous and arterial portions of the blood circuit are parallel channels.

Further twenty-fifth embodiments include ones in which the venous and arterial portions of the blood circuit are parallel tubes over a major fraction thereof.

Further twenty-fifth embodiments include ones in which temperature sensor is an active temperature sensor that measures temperature by actively canceling heat flux in a wall of the blood circuit separating the temperature sensor from the blood whose temperature is to be measured.

Further twenty-fifth embodiments include ones in which the controller calculates a heat transfer parameter of the blood circuit, the heat transfer parameter is responsive to a thermal resistance of a wall of the blood circuit According to twenty-sixth embodiments, the disclosed subject matter includes, a system for performing a blood treatment. A blood treatment machine is adapted to receive a blood circuit and for pumping blood from a patient. A controller is connected to the blood treatment machine, the controller is programmed to pump blood at multiple flow rates during a predetermined operating mode. During the predetermined operating mode, the controller measures blood temperatures, and recording them, so that the blood temperatures are measured in the blood circuit at a first temperature sensor located remote from a patient access of the blood circuit, the patient access is connected by an arterial portion thereof to the temperature sensor, the blood temperatures is measured and recorded for each of the multiple flow rates. The controller calculates a heat transfer characteristic of the blood circuit from the patient access to the first temperature sensor responsively to the multiple flow rates and the respective temperatures. The controller, responsively to the heat transfer characteristic, regulates a return temperature at a patient access end of a venous portion of the blood circuit that returns blood to the patient.

Further twenty-sixth embodiments include ones in which the regulating is effective to maintain a body temperature of a patient in a predefined range.

Further twenty-sixth embodiments include ones in which the regulating includes compensating for heat transfer in the venous portion between blood carried thereby and an external environment of the venous portion.

Further twenty-sixth embodiments include ones in which the controller is further programmed for detecting a condition indicating that the heat transfer characteristic has changed and, responsively thereto, repeating the pumping blood at multiple flow rates and calculating a heat transfer characteristic responsively to a result of the detecting.

Further twenty-sixth embodiments include ones in which the detecting a condition includes a predefined change in the temperature indicated by the first temperature sensor.

Further twenty-sixth embodiments include ones in which the detecting includes detecting a mechanical movement of the blood circuit.

Further twenty-sixth embodiments include ones in which the controller is further programmed for detecting a steady state of the heat transfer characteristic, wherein the recording is responsive to the detecting a stead state.

According to twenty-seventh embodiments, the disclosed subject matter includes, a blood treatment system, capable of calculating a patient blood temperature. An extracorporeal blood processing machine is adapted for pumping blood from a patient, a controller controlling the extracorporeal processing machine to pump blood at multiple flow rates during a predefined operating mode. The controller measures blood temperatures in a blood circuit at a first temperature sensor located remote from a patient access of a blood circuit. The patient access is connected by an arterial portion of the blood circuit to the first temperature sensor. The controller measures and records the blood temperatures for each of the multiple flow rates. The controller calculates a heat transfer characteristic of the blood circuit from the patient access to the first temperature sensor responsively to the multiple flow rates and the respective temperatures. The controller, responsively to the heat transfer characteristic, calculates a patient body temperature by compensating for heat transfer between the patient access and the temperature sensor based on the heat transfer characteristic.

Further twenty-seventh embodiments include ones in which the heat transfer characteristic is responsive to a heat transfer coefficient and a temperature of an environment of the arterial portion.

Further twenty-seventh embodiments include ones in which the body temperature is stored by the controller to a treatment log corresponding to each of multiple patients.

Further twenty-seventh embodiments include ones in which the controller output a signal responsively to a comparison between data in the treatment log and a temperature resulting from the calculating.

Further twenty-seventh embodiments include ones in which the controller stores the body temperature to a treatment log corresponding to each patient includes a time series of temperatures over an interval of a treatment.

Further twenty-seventh embodiments include ones in which the controller outputs a signal responsive to a comparison between data in the treatment log and a temperature resulting from the calculating.

Further twenty-seventh embodiments include ones in which the controller repeats again pumps blood at multiple flow rates and calculates a heat transfer characteristic of the blood circuit in response to the lapse of a timer.

Further twenty-seventh embodiments include ones in which the controller repeats again pumps blood at multiple flow rates and calculates a heat transfer characteristic of the blood circuit in response to the lapse of a timer initialized at the beginning of a blood treatment.

The embodiments include any method, device, or system of any of the foregoing embodiments wherein any recited calculations are performed by the controller of a blood processing machine.

In any of the foregoing embodiments in which $T_p$ is first calculating from the assumption of a constant heat transfer rate (power units) and then revised iteratively based on an assumed (or calculated $T_a$, the initial value of $T_p$ can, instead, be simply guessed. For example, in the methods of FIGS. 15A, 15B, and 15C, the step S64' may be followed instead of step S64. The value of $T_p$ will eventually converge to the same value. Any of the claims may be modified to guess an initial value of the recited core temperature, inlet temperature or $T_p$ according to how the temperature is identified in the claim.

It will be appreciated that the modules, processes, systems, and sections described above can be implemented in hardware, hardware programmed by software, software instruction stored on a non-transitory computer readable medium or a combination of the above. For example, a method for calculating human core temperature, blood temperature, or temperature of fluid in any vessel can be implemented, for example, using a processor configured to execute a sequence of programmed instructions stored on a non-transitory computer readable medium. For example, the processor can include, but not be limited to, a personal computer or workstation or other such computing system that includes a processor, microprocessor, microcontroller device, or is comprised of control logic including integrated circuits such as, for example, an Application Specific Integrated Circuit (ASIC). The instructions can be compiled from source code instructions provided in accordance with a programming language such as Java, C++, C#.net or the like. The instructions can also comprise code and data objects provided in accordance with, for example, the Visual Basic™ language, LabVIEW, or another structured or object-oriented programming language. The sequence of programmed instructions and data associated therewith can be stored in a non-transitory computer-readable medium such as a computer memory or storage device which may be any suitable memory apparatus, such as, but not limited to read-only memory (ROM), programmable read-only memory (PROM), electrically erasable programmable read-only memory (EEPROM), random-access memory (RAM), flash memory, disk drive and the like.

Furthermore, the modules, processes, systems, and sections can be implemented as a single processor or as a distributed processor. Further, it should be appreciated that the steps mentioned above may be performed on a single or distributed processor (single and/or multi-core). Also, the processes, modules, and sub-modules described in the various figures of and for embodiments above may be distributed across multiple computers or systems or may be co-located in a single processor or system. Exemplary structural embodiment alternatives suitable for implementing the modules, sections, systems, means, or processes described herein are provided below.

The modules, processors or systems described above can be implemented as a programmed general purpose computer, an electronic device programmed with microcode, a hard-wired analog logic circuit, software stored on a computer-readable medium or signal, an optical computing device, a networked system of electronic and/or optical devices, a special purpose computing device, an integrated circuit device, a semiconductor chip, and a software module or object stored on a computer-readable medium or signal, for example.

Embodiments of the method and system (or their sub-components or modules), may be implemented on a general-purpose computer, a special-purpose computer, a programmed microprocessor or microcontroller and peripheral integrated circuit element, an ASIC or other integrated circuit, a digital signal processor, a hardwired electronic or logic circuit such as a discrete element circuit, a programmed logic circuit such as a programmable logic device (PLD), programmable logic array (PLA), field-programmable gate array (FPGA), programmable array logic (PAL) device, or the like. In general, any process capable of implementing the functions or steps described herein can be used to implement embodiments of the method, system, or a computer program product (software program stored on a non-transitory computer readable medium).

Furthermore, embodiments of the disclosed method, system, and computer program product may be readily implemented, fully or partially, in software using, for example, object or object-oriented software development environments that provide portable source code that can be used on a variety of computer platforms. Alternatively, embodiments of the disclosed method, system, and computer program product can be implemented partially or fully in hardware using, for example, standard logic circuits or a very-large-scale integration (VLSI) design. Other hardware or software can be used to implement embodiments depending on the speed and/or efficiency requirements of the systems, the particular function, and/or particular software or hardware system, microprocessor, or microcomputer being utilized. Embodiments of the method, system, and computer program product can be implemented in hardware and/or software using any known or later developed systems or structures, devices and/or software by those of ordinary skill in the applicable art from the function description provided herein and with a general basic knowledge of sensor, controller, and/or processor systems and/or computer programming arts.

Moreover, embodiments of the disclosed method, system, and computer program product can be implemented in software executed on a programmed general purpose computer, a special purpose computer, a microprocessor, or the like.

It is, thus, apparent that there is provided, in accordance with the present disclosure, temperature measurement devices, methods, and systems. Many alternatives, modifications, and variations are enabled by the present disclosure. Features of the disclosed embodiments can be combined, rearranged, omitted, etc., within the scope of the invention to produce additional embodiments. Furthermore, certain features may be used without a corresponding use of other features. Accordingly, Applicant intends to embrace all such alternatives, modifications, equivalents, and variations that are within the spirit and scope of the present invention.

What is claimed is:

1. A method of detecting a fever in a patient undergoing extracorporeal blood processing, comprising:
controlling, using an automatic controller, a rate of flow of blood through a flow channel connecting the patient to a temperature sensor, to establish a first flow rate;
at the first flow rate, permitting the flow of an unknown quantity of heat to or from the flow channel connecting the patient to the temperature sensor;

at the first flow rate, measuring at least one temperature of the flow channel using the temperature sensor;

recording first temperature data responsively to said measuring;

controlling, using the automatic controller, the rate of the flow of the blood through the flow channel to establish a second flow rate, different from the first flow rate;

repeating the permitting and measuring at the second flow rate and recording a second temperature data responsively to the corresponding measuring;

calculating an inferred temperature from the first temperature data and the second temperature data, the inferred temperature representing a temperature remote from the temperature sensor; and comparing the inferred temperature to data responsive to at least one reference temperature and outputting the data to a user interface indicating the data responsive to a result of said comparing.

2. The method of claim 1, wherein the controlling to establish includes holding constant the respective first and second flow rates for a period of time effective to establish an unchanging temperature indicated by said temperature sensor.

3. The method of claim 1, wherein the flow channel is an arterial line.

4. The method of claim 1, wherein said controlling to establish the first flow rate and said controlling to establish the second flow rate include flowing at a respective rate for an interval effective to establish a steady state temperature indicated by said temperature sensor.

5. The method of claim 1, wherein the flow channel is an arterial line of an extracorporeal blood circuit.

6. The method of claim 1, wherein the permitting includes permitting the flow of heat from the flow channel to an ambient environment through a blood-carrying tube.

7. A method of detecting a fever in a patient undergoing extracorporeal blood processing, comprising:

controlling, using an automatic controller, a rate of flow of blood through a flow channel connecting the patient to a temperature sensor to establish a first flow rate;

at the first flow rate, permitting the flow of an unknown quantity of heat to or from the flow channel connecting the patient to the temperature sensor;

at the first flow rate, minimizing a flow of heat from or to the flow channel at the temperature sensor and while measuring at least one temperature of the flow channel using the temperature sensor, the minimizing including actively regulating a heat flux to minimize the heat flux from the flow channel through the temperature sensor;

recording a first temperature data responsively to said measuring;

controlling, using the automatic controller, the rate of the flow of the blood through the flow channel to establish a second flow rate, different from the first flow rate;

repeating the permitting, minimizing, and measuring at the second flow rate and recording a second temperature data responsively to the corresponding measuring;

calculating an inferred temperature from the first and second temperature data, the inferred temperature representing a temperature remote from the temperature sensor; and comparing the inferred temperature to data responsive to at least one reference temperature and outputting the data to a user interface indicating the data responsive to a result of said comparing.

8. The method of claim 7, wherein the controlling to establish the second flow rate includes holding the respective first and second flow rates for a period of time effective to establish an unchanging temperature indicated by said temperature sensor.

9. The method of claim 7, wherein the flow channel is an arterial line.

10. The method of claim 7, wherein said controlling to establish the first flow rate and said controlling to establish the second flow rate include flowing at a respective rate for an interval effective to establish a steady state condition in terms of heat flow into or out of the flow channel.

11. The method of claim 7, wherein the flow channel is a venous line.

12. The method of claim 7, wherein the permitting includes permitting the flow of heat from the flow channel to an ambient environment through a blood carrying tube.

13. The method of claim 7, wherein the data responsive to a condition includes data indicating that the patient has the fever.

14. A blood treatment system for treating a patient, comprising:

a blood treatment machine having a programmable controller and at least a blood pump whose pumping rate is controlled by the controller;

the blood treatment machine being arranged to receive a disposable blood circuit, the blood treatment machine having a temperature sensor positioned on the blood treatment machine to measure a temperature of blood flowing through the disposable blood circuit attached to the blood treatment machine;

the controller being programmed to establish a flow of the blood at a first rate according to a first predefined condition, whereupon the controller records first temperature data representing the temperature indicated by said temperature sensor;

the controller being programmed subsequently to establish the flow of the blood at a second rate according to a second predefined condition, whereupon the controller records second temperature data representing the temperature indicated by said temperature sensor;

the controller being further programmed to calculate patient temperature data indicating the temperature of the disposable blood circuit responsively to both said first and second temperature data; and the controller being further programmed to output a patient temperature signal to a user interface responsively to said patient temperature data.

15. The blood treatment system of claim 14, wherein the patient temperature signal includes an indication that the patient has a fever.

16. The blood treatment system of claim 14, wherein the controller compares the patient temperature data to a predefined range and said patient temperature signal is responsive to a result of such a comparison.

17. The blood treatment system of claim 14, wherein the first predefined condition and the second predefined condition are time intervals.

18. The blood treatment system of claim 14, wherein the first predefined condition and the second predefined condition are identical time intervals.

19. The blood treatment system of claim 14, wherein the first predefined condition and the second predefined condition include a detected establishment of unchanging temperature indicated by said temperature sensor and determined by the controller.

20. The blood treatment system of claim 14, wherein the temperature sensor is a contact-type temperature sensor that has a surface temperature element that engages an outside of the disposable blood circuit when it is attached to the blood treatment machine.

\* \* \* \* \*